United States Patent
Oklu et al.

(10) Patent No.: US 12,246,086 B2
(45) Date of Patent: Mar. 11, 2025

(54) APPLICATIONS AND IMAGING OF SHEAR-THINNING BIOMATERIAL

(71) Applicants: MAYO FOUNDATION FOR MEDICAL EDUCATION AND RESEARCH, Rochester, MN (US); The Regents of the University of California, Oakland, CA (US); Boston Scientific Scimed, Inc., Maple Grove, MN (US)

(72) Inventors: Rahmi Oklu, Chandler, AZ (US); Hassan Albadawi, Phoenix, AZ (US); Amir Sheikhi, State College, PA (US); Ali Khademhosseini, Los Angeles, CA (US); Ehsan Jabbarzadeh, Columbia, SC (US)

(73) Assignees: MAYO FOUNDATION FOR MEDICAL EDUCATION AND RESEARCH, Rochester, MN (US); The Regents of the University of California, Oakland, CA (US); Boston Scientific Scimed, Inc., Maple Grove, MN (US)

( * ) Notice: Subject to any disclaimer, the term of this patent is extended or adjusted under 35 U.S.C. 154(b) by 773 days.

(21) Appl. No.: 17/442,444

(22) PCT Filed: Mar. 26, 2020

(86) PCT No.: PCT/US2020/025009
§ 371 (c)(1),
(2) Date: Sep. 23, 2021

(87) PCT Pub. No.: WO2020/198504
PCT Pub. Date: Oct. 1, 2020

(65) Prior Publication Data
US 2022/0192974 A1    Jun. 23, 2022

Related U.S. Application Data

(60) Provisional application No. 62/824,175, filed on Mar. 26, 2019.

(51) Int. Cl.
*A61K 9/00* (2006.01)
*A61F 6/06* (2006.01)

(52) U.S. Cl.
CPC .............. *A61K 9/0034* (2013.01); *A61F 6/06* (2013.01); *A61K 9/0024* (2013.01)

(58) Field of Classification Search
None
See application file for complete search history.

(56) References Cited

U.S. PATENT DOCUMENTS

2018/0185096 A1* 7/2018 Eisenfrats .......... A61B 17/1219
2018/0360920 A1* 12/2018 Khademosseini .. A61L 24/0015

FOREIGN PATENT DOCUMENTS

WO    2017/069822         4/2017
WO    WO-2017069822 A2 *  4/2017 ............. A61K 38/39

OTHER PUBLICATIONS

PCT International Search Report & Written Opinion dated Jul. 3, 2020 for PCT Application No. PCT/US2020/025009.

* cited by examiner

*Primary Examiner* — Brian Gulledge
(74) *Attorney, Agent, or Firm* — Seager, Tufte, & Wickhem, LLP

(57) ABSTRACT

Systems and methods of using and imaging shear-thinning biomaterial compositions are provided. More particularly, systems and methods of providing reversible birth control and/or for delivering therapeutics to reproductive organs are provided. A method includes administering a biomaterial (Continued)

into fallopian tubes, uterus, or vas deferens of the subject, where the biomaterial is a shear-thinning nanocomposite.

19 Claims, 21 Drawing Sheets

| Optimization of Laponite (L)–PEO (P) STB rheology: X = liquid, Y = injectable gel, Z = uninjectable gel | | | | |
|---|---|---|---|---|
| Concentration | L4% | L5% | L6% | L7% |
| P1% | X | Y | Y | Z |
| P3% | X | Y | Y | Z |
| P5% | X | Y | Y | Z |
| P10% | X | Z | Z | |

APPLICATIONS AND IMAGING OF SHEAR-THINNING BIOMATERIAL

CROSS-REFERENCE TO RELATED APPLICATIONS

This application is based on, claims priority to, and incorporates herein by reference in its entirety, U.S. Provisional Patent Application Ser. No. 62/824,175, filed on Mar. 26, 2019.

STATEMENT REGARDING FEDERALLY FUNDED RESEARCH

N/A.

BACKGROUND

Various methods of birth control exist. One popular method of reversible birth control in females is an intrauterine device (IUD). An IUD is a small device (often T-shaped) that is inserted into the uterine cavity and works, in part, by blocking sperm mobility through the fallopian tubes. In some cases, however, the IUD may migrate away from its ideal position at the top of the uterus, reducing the effectiveness of the device and potentially resulting in expulsion. Furthermore, in some cases, the IUD may perforate the uterus and invasive surgery may be required to remove the device. The risk of these side effects may increase based on the orientation of the subject's uterus (e.g., if the uterus is retroverted).

Alternatives to the IUD also exist for birth control. Some devices, including the Essure® device, irreversibly prevent pregnancy. The Essure® device is a small, spring-like structure that includes polyethylene terephthalate (PET) fibers surrounding its outer surface. Before it is inserted, the spring-like structure is tightly coiled and placed into a catheter. Once the catheter is loaded with the device, the catheter is placed into the fallopian tube of a subject. The device is then released from the catheter, causing the tightly-coiled device to expand and conform to the fallopian tube lumen. The PET fibers surrounding the outer surface of the device contact the lumen of the fallopian tube and elicit tissue growth. This tissue growth occludes the fallopian tube, effectively preventing both an egg from reaching the implantation site and sperm from reaching the egg, thus preventing pregnancy. However, along with the potentially undesirable consequence of irreversible birth control, the Essure® device includes multiple risks and hazards, such as pain, allergic reactions, perforation of the uterus or fallopian tubes, and, most notably, placement failure or failure of the device to prevent pregnancy.

Furthermore, many male birth control techniques currently exist, such as a vasectomy. During this procedure, the vas deferens is surgically tied or excised to prevent sperm from traveling to the urethra and, thus, inhibiting sperm from reaching the female reproductive system during intercourse. A vasectomy procedure is challenging to reverse, and reversal attempts are often met with limited success. For example, reversal of a vasectomy often requires multiple surgical interventions, carrying inherent risks. Additionally, other male birth control techniques include male birth contraceptives agents, which can be steroid-based compounds that pharmacologically suppress sperm production and require the subject to receive a daily pill or topically apply a gel. However, these techniques bare the risk of potential hormonal-mediated side effects.

SUMMARY

The present disclosure relates to systems and methods of using and imaging shear-thinning biomaterial compositions, and more particularly, to systems and methods of using shear-thinning biomaterials for providing reversible birth control and/or for delivering therapeutics to reproductive organs.

In accordance with one aspect of the disclosure, a method of reversible birth control in a subject is provided. The method includes administering a biomaterial into fallopian tubes, uterus, or the scrotal vas deferens of the subject, where the biomaterial is a shear-thinning nanocomposite.

In accordance with another aspect of the disclosure, a method of delivering a therapeutic agent to a reproductive organ of a subject is provided. The method includes administering a biomaterial to the reproductive organ, where the biomaterial includes a shear-thinning nanocomposite in combination with the therapeutic agent.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1A illustrates a general make-up of a nancomposite composition for use in a subject; FIG. 1B illustrates a chart of tested nancomposite compositions having different formulations; FIG. 1C illustrates a nancomposite composition with desired physical properties for use with aspects of the disclosure; FIG. 1D illustrates a graph of shear rate versus viscosity of tested nancomposite compositions; FIG. 1E illustrates a graph of stress versus storage moduli of tested nancomposite compositions; FIG. 1F illustrates a graph of concentration versus storage moduli of tested nancomposite compositions at different temperatures; and FIG. 1G illustrates time versus storage modulus and plastic modulus of a tested nancomposite composition following intermittent shear strain.

FIG. 3A illustrates a sample injection testing setup; FIG. 3B illustrates a graph of injection time versus injection force; FIG. 3C illustrates a graph of incubation time versus injection force; FIG. 3D illustrates a graph of time versus swelling ratio in a first tested media; FIG. 3E illustrates a graph of time versus swelling ratio in a second tested media; FIG. 3F illustrates a graph of time versus remaining mass; FIG. 3G illustrates a sample compression testing setup; FIG. 3H illustrates a graph of compressive strain versus compressive stress; FIG. 3I illustrates a graph of composition versus compressive modulus; FIG. 3J illustrates a sample strength testing setup;

FIG. 3K illustrates a graph of composition versus adhesion strength; and FIG. 3L illustrates a graph of composition versus failure load.

FIG. 4A illustrates female reproductive anatomy; FIG. 4B is a chart of tested sample tubes and respective properties; FIG. 4C illustrates a sample pressure test setup; and FIG. 4D illustrates a graph of tube diameter versus occlusion pressure.

FIGS. 7A, 7B, 7C, and 7D illustrate a series of x-ray images of a subject's uterus during insertion of a biomaterial into a subject's fallopian tube.

DETAILED DESCRIPTION

Figure 1A:
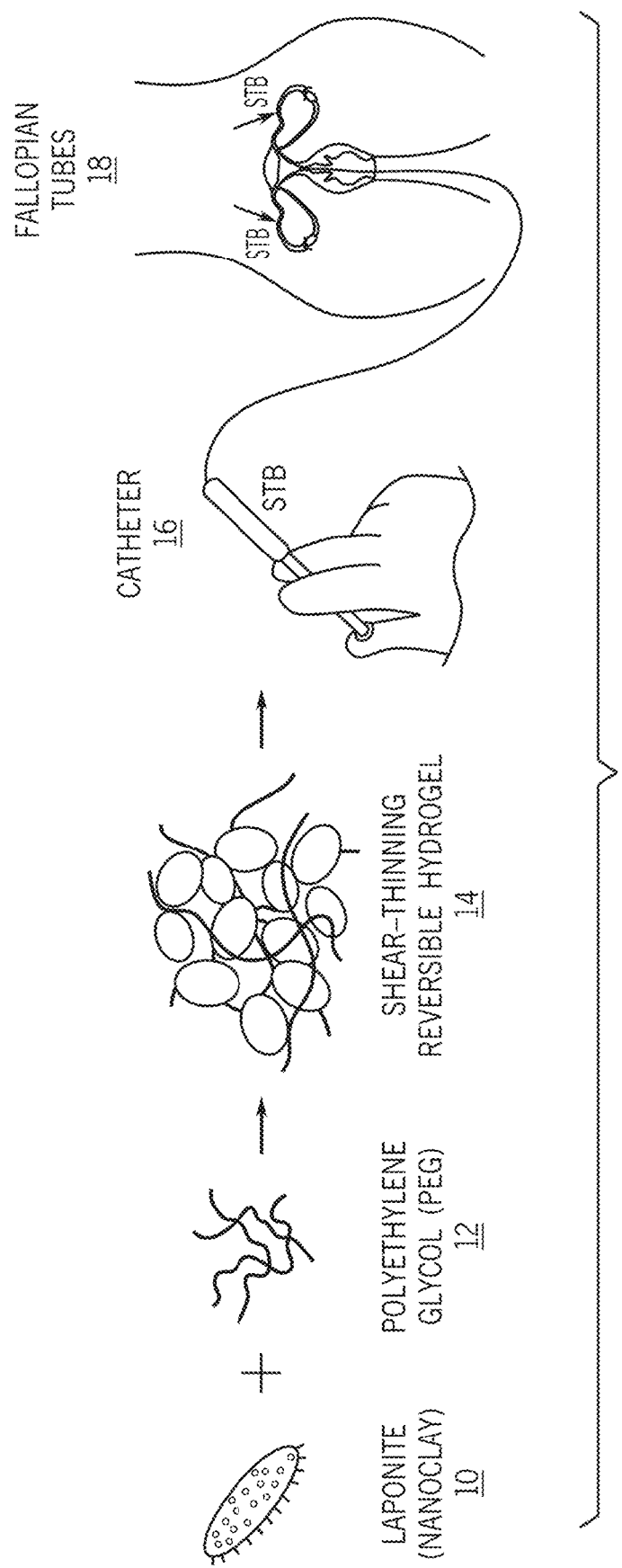
FIGS. 1A-1G illustrate example preparation and testing of various nanocomposite compositions, where

The present disclosure provides applications and imaging for shear-thinning nanocomposites and, more specifically, shear-thinning biomaterials (STBs). According to some applications, the present disclosure provides systems and methods for reversible birth control using shear-thinning biomaterials and, more specifically, systems and methods comprising administering to a subject, via the subject's intrauterine cavity or the vas deferens, a therapeutically effective amount of a shear-thinning biomaterial.

A unique material property of nanocomposites is their ability to exhibit shear-thinning capabilities. For example, shear-thinning nanocomposites, especially biomaterial nanocomposites, can change material state from gel-like to solid based on an applied shear pressure. More specifically, a shear-thinning nanocomposite becomes "thinned" and is able to flow in a gel-like state when adequate shear force is applied to it. Once the force is removed, the composition is able to recover its previous substantially solid material properties in order to remain stable in its new environment, and also to remain resistant to physiological degradation or mechanical forces that could disrupt the composition. Thus, "shear-thinning" or "shear-thinning behavior" refers to a decrease in viscosity (i.e., increase in flow rate) of a composition with increasing application of shear stress.

Accordingly, in some embodiments, due to the shear-thinning behavior of the composition of some embodiments, the applied pressure causes the composition to transform to a gel-like state and flow through the subject's reproductive anatomy. The composition can exhibit a decrease in viscosity (i.e., increase in flow) upon application of an increasing rate of shear stress during administration. Furthermore, due to its gel-like state, when inserted into a space, the composition can fill the insertion space. Thus, when administered, the composition can conform to the shape of, for example, a fallopian tube, uterus, or vas deferens of the subject. Additionally, generally, the compositions provided herein may flow with minimal applied pressure during injection, thus providing a method of administration that avoids additional trauma to the subject.

The present disclosure accordingly provides a nanocomposite that can be a nanoengineered shear-thinning hydrogel. The shear-thinning composite can be a biomaterial that is biocompatible and nontoxic (and, thus, may be referred to as a shear-thinning biomaterial). As such, herein, the terms shear-thinning nanocomposite, shear-thinning composition, nanocomposite composition, shear-thinning biomaterial, STB, and shear-thinning hydrogel may be used interchangeably.

In some embodiments, the composition can comprise gelatin, or a derivative thereof, and silicate nanoparticles. One example of silicate nanoparticles includes Laponite® (lithium magnesium sodium silicate), a commercially available nanoclay. In other embodiments, a shear-thinning composition comprises a gelatin, or a derivative thereof, silicate nanoparticles, and water (such as deionized water). In other embodiments, a shear-thinning composition comprises a gelatin, or a derivative thereof, silicate nanoparticles, and/or a polymer such as polyethylene oxide (PEO, or polyethylene glycol, PEG) or another polymer. For example, composition combinations can include, but are not limited to: silicate nanoparticles-gelatin, silicate nanoparticles-PEO, silicate nanoparticles-hyaluronic acid, silicate nanoparticles-poly (N-isopropylacrylamide), etc. Furthermore, as further discussed below, compositions may also include a contrast or imaging agent.

Accordingly, in one particular example, the nanocomposite can be made up of Laponite (BYK Additives & Instruments), and a PEO (e.g., molecular weight of about 20,000; Sigma Aldrich). In some examples, PEO may have a molecular weight in the range of about 10,000 to about 30,000. Additional example compositions for use with embodiments of the present invention are described in International Publication No. WO2017/069822, the entire disclosure of which is incorporated herein by reference.

Generally, in some applications, nanocomposite compositions can comprise silicate nanoparticle (e.g., Laponite) concentrations between about 0.5% to about 10.0% weight by volume ("w/v") and, more particularly, between about 1.0% to about 5.0% w/v. The nanocomposite compositions can further comprise PEO concentrations between about 4.0% and about 7.0% and, more particularly, between about 5.0% and about 6.0%. The physical, mechanical, and biological properties of the nanocomposite of some applications can be selected in accordance with the discussion below. In the examples below and corresponding figures, nanocomposite compositions are illustrated and discussed as a combination of a concentration of Laponite and a concentration of PEO (e.g., in terms of w/v). In some instances, each composition has an "L" followed by a number, and a "P" followed by a number. This indicates that the specific nanocomposite has a concentration of L (Laponite) designated by the number following it, and a concentration of P (PEO) designated by the number following it. For example, "L5P1" has a concentration of 5% L and a concentration of 1% PEO. If the specific injectable nanocomposite does not have an L or a P (e.g., "L5", or "L6"), this means that the specific injectable nanocomposite does not contain L or P, respectively. For example, "L5" has a concentration of 5% L with no PEO present.

In accordance with some embodiments, FIGS. 1A-1G illustrate example preparation and testing of various nanocomposite compositions. For example, FIG. 1A illustrates how a nanocomposite can be prepared and used as a form of female birth control. In some embodiments, Laponite 10 and PEO 12 (or PEG), each having a specific concentration, can be mixed to form a shear-thinning reversible hydrogel, or STB, 14. The nanocomposite can then be injected (e.g., via a catheter 16, such as a size 4 French gauge (Fr) or a size 5 Fr catheter) into one or both of a patient's fallopian tubes 18. The injected nanocomposite can provide a physical barrier within the fallopian tube 18, and thus prevents sperm-oocyte fusion in mammals. More specifically, the nanocomposite barrier can block oocytes from traveling down the fallopian tube 18, therefore preventing sperm from reaching the oocyte.

Figures 1B, 1C:
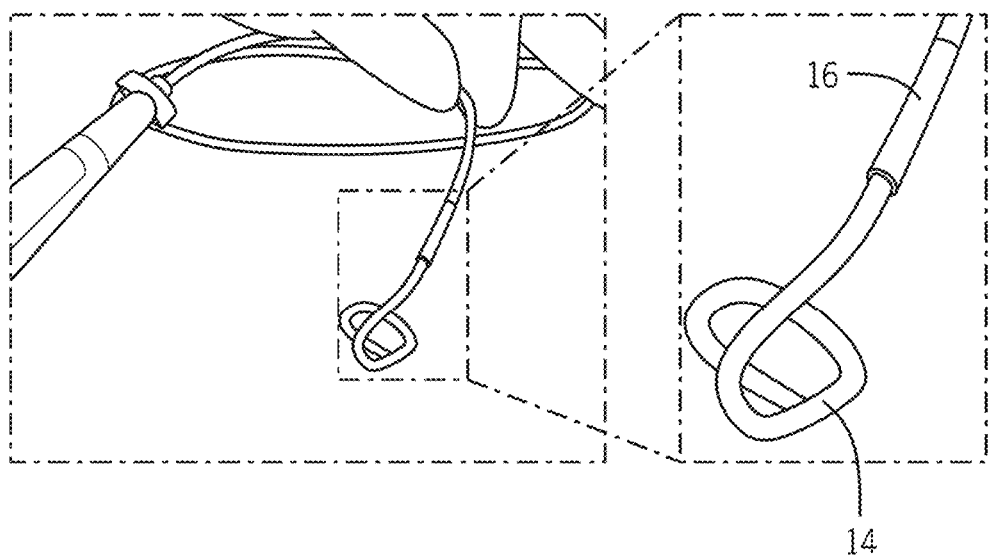

In some applications, an injectable and mechanically resilient nanocomposite can be desirable. FIG. 1B illustrates various candidates for a nanocomposite composition, based on injectibility testing using a 4 F (0.035-inch), 65-cm catheter. The candidates include nanocomposite compositions ranging from L4% to L7% and from P1% to P10% (that is, L4P1, L4P3, L4P5, L4P10, L5P1, L5P3, L5P5, L5P10, L6P1, L6P3, L6P5, L6P10, L7P1, L7P3, and L7P5). For example, as shown in FIG. 1B, the cell in the first row and first column of FIG. 1B designates a nanocomposite composition containing a PEO concentration of 1% and an L concentration of 4%. In FIG. 1B, the nanocomposite compositions designated by an "X" indicate that the nanocomposite composition may be too mushy or liquid for use in certain applications. The nanocomposite compositions designated by a "Z" indicate that the nanocomposite composition may be too solid for use in certain applications. The nanocomposite compositions designated by a "Y" indicate that the nanocomposite composition may be injectable (e.g., not too liquid or solid, and displaying shear-thinning material properties). Based on the test results illustrated in FIG. 1B, in some applications, a suitable injectable nanocomposite composition may have a concentration of 5-6% L and a concentration of 1-5% PEO. However, other concentrations may be contemplated within the scope of this disclosure.

As shown in FIG. 1O, a "Y" nanocomposite composition from FIG. 1B (herein, "injectable nanocomposites") can be easily injectable through a 5 Fr catheter 16, thus providing a self-standing hydrogel construct 14 after exiting the catheter tip. For example, in the inset of FIG. 1O, the 5 Fr catheter highlights an extruded injectable nanocomposite 14, according to some embodiments.

Figure 1D:
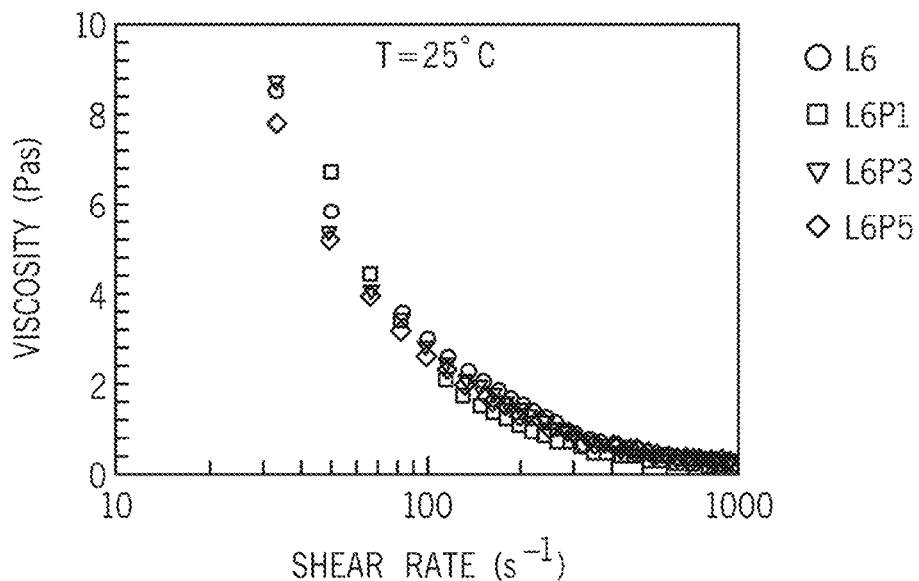

FIGS. 1D-1G illustrate results of testing in accordance with FIGS. 1A-1C of injectable nanocomposites containing 6% L and various PEO concentrations (0%, 1%, 3%, and 5%). More specifically, FIG. 1D illustrates dynamic viscosity (in Pascal-Seconds, Pa-s) versus shear rate (per second, $s^{-1}$) of the tested injectable nanocomposites. As shown in FIG. 1D, the injectable nanocomposite demonstrates a non-Newtonian behavior for fluid and, more specifically, possesses shear-thinning properties (e.g., as the shear rate increases, the viscosity decreases).

Figure 1E:
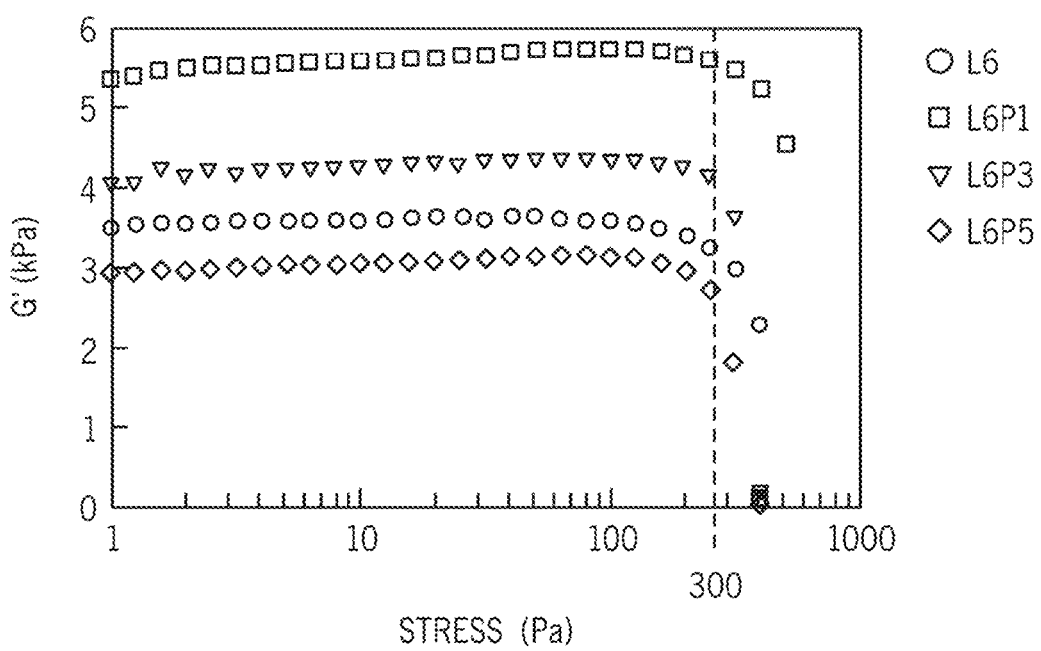

FIG. 1E illustrates a graph of the storage moduli (G', in kiloPascals, kPa) of the tested injectable nanocomposite calculated by subjecting each injectable nanocomposite to a broad range of oscillatory stresses (in Pascals, Pa), at room temperature. This can indicate that the injectable nanocomposite displays a linear viscoelasticity and a solid-like behavior at a shear stress below 300 Pa. Accordingly, a shear stress greater than 300 Pa would be needed to transform the injectable nanocomposite into a gel-like state for, for example, administration to a subject's reproductive anatomy.

Figure 1F:
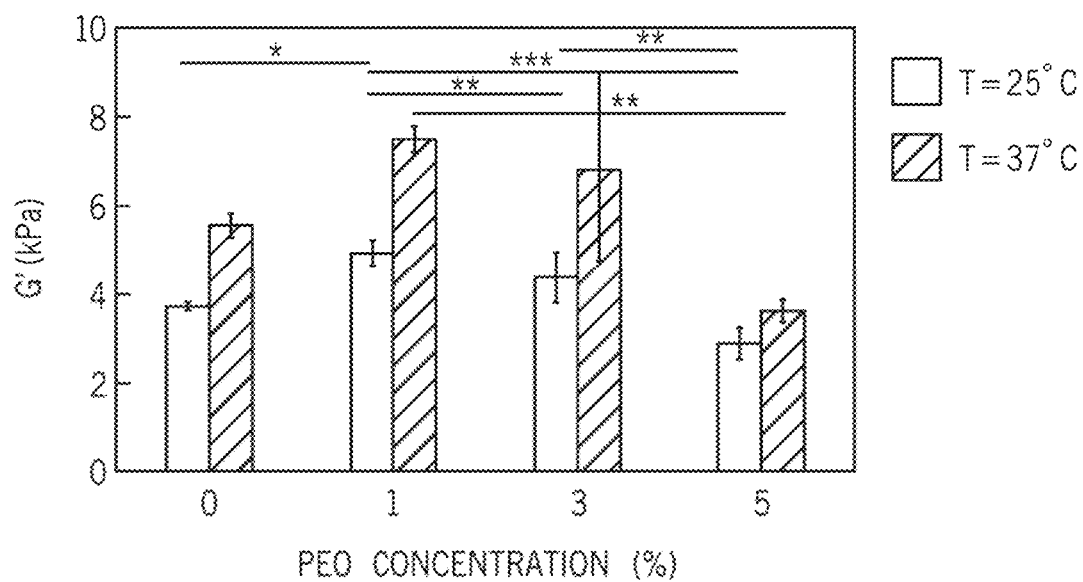

FIG. 1F illustrates the effect of PEO concentration and temperature on the storage moduli of the tested injectable nanocomposites. Each of these injectable nanocomposites was subjected to an oscillatory frequency ("ω") of ~10 rad s-1. This can indicate that the most noticeable elastic behavior of an injectable nanocomposite occurs at PEO concentrations of ~1-3%.

Figure 1G:
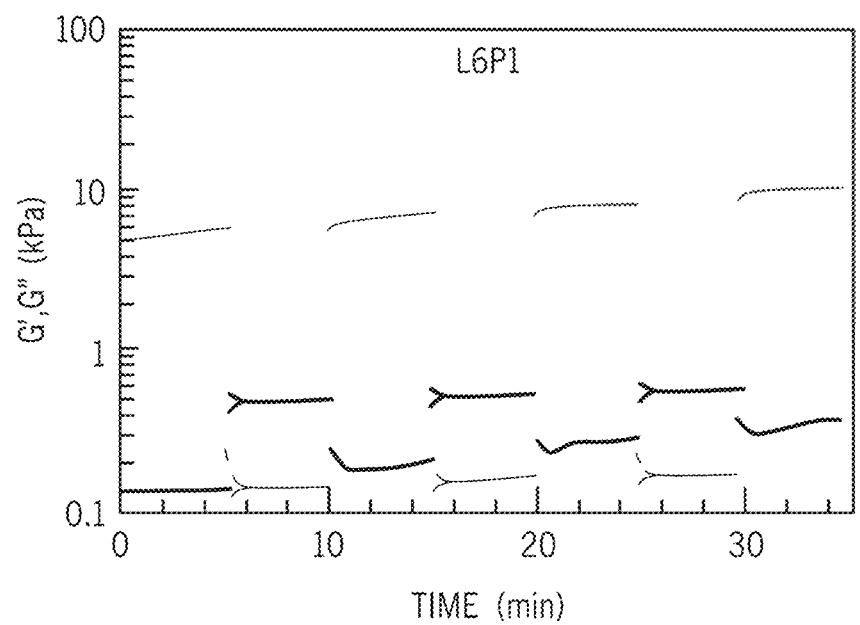

FIG. 1G illustrates the cyclic recovery of one of the tested injectable nanocomposites (with concentrations of 6% L and 1% PEO). Specifically, this injectable nanocomposite was subjected to an intermittent shear strain of ~100% and storage module (G') and plastic modulus (G") were observed. This may attest to the injectable nanocomposite's solid-like behavior at rest, where the storage modulus is greater than the plastic modulus (e.g., where G'>G", at 0-5 min, 10-15 min, 20-25 min, 30-35 min). This may also attest to the injectable nanocomposite's liquid-like behavior under shear, where the plastic modulus is greater than the storage modulus (e.g., where G">G', at 5-10 min, 15-20 min, 25-30 min).

Additionally, testing was performed to illustrate the stability of an injectable nanocomposite during physiological conditions, and its reversibility when placed in deionized water. For example, in some embodiments, the injectable nanocomposite can be more stable in physiological conditions, such as phosphate buffered saline ("PBS") and human tubal fluid ("HTF"). Furthermore, in some embodiments, the injectable nanocomposite can be readily dispersed in deionized water.

According to this testing, various compositions of injectable nanocomposites, having various combinations of concentrations of L and PEO, were shaped as a disc (diameter ~1.5 cm, height ~0.3 cm) and placed in a corresponding dish. Images were taken and observed of each injectable nanocomposite composition (ranging from 5% L to 6% L and 0% PEO to 5% PEO, including L5, L5P1, L5P3, L5P5, L6, L6P1, L6P3, and L6P5) at various time intervals of incubation: 0 hour (h), 1 h, 5 h, 12 h, 72 h, 1 week (w), 2 w, 3 w, 4, w, 5 w, 6 w, and 8 w.

In a first test for stability in PBS, each of the injectable nanocomposite compositions were incubated in PBS at 37° C. According to this example, the injectable nanocomposite compositions having a concentration of 5% L displayed rapid disintegration, while other injectable nanocomposite compositions (such as those at L6P1 and L6P3) were found to be highly stable up to the full eight weeks.

In a second test for stability in HTF, the best performing injectable nanocomposite compositions in PBS from the first test (i.e., L6, L6P1, L6P3) were incubated in HTF. Images were taken and observed of each injectable nanocomposite at various time intervals of incubation: 0 h, 1 h, 2 h, 4 h, 10 h, 24 h, 48 h, 96, h, 1 w, 2 w, 3 w, 4, w, and 5 w. According to this example, the three selected injectable nanocomposite compositions also remained stable over time in HTF.

Figure 2:
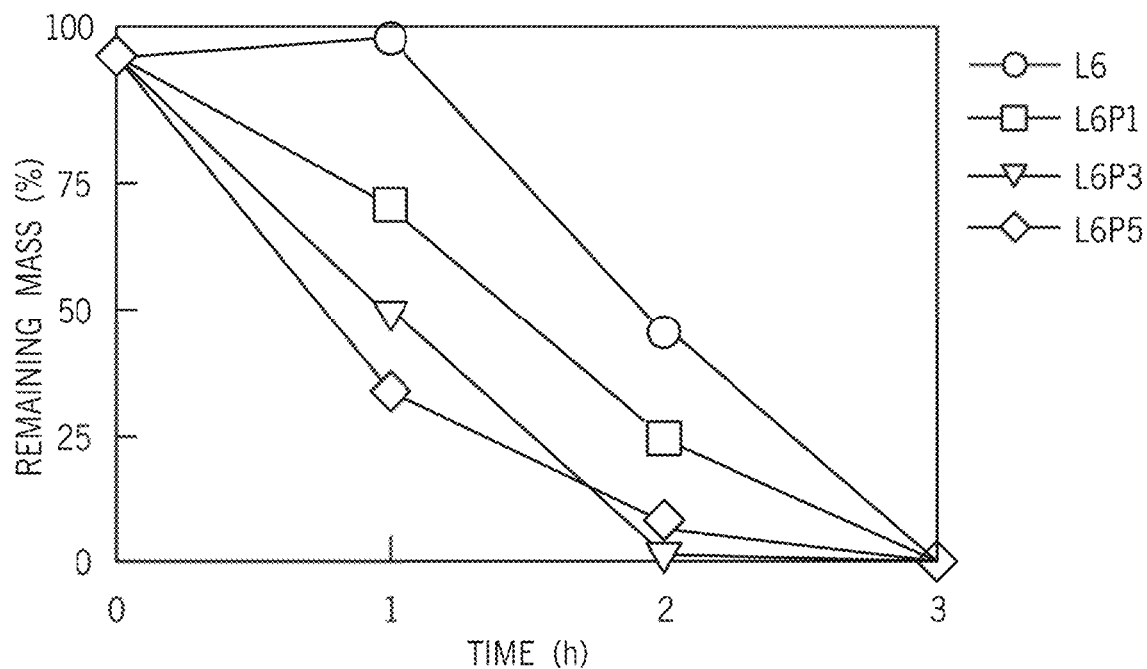
FIG. 2 illustrates results indicating the stability of various nanocomposite compositions and, more specifically, a graph showing time versus remaining mass.

FIG. 2 illustrates the results of example stability testing of injectable nanocomposites when placed in deionized water. According to this example, when the injectable nanocomposite compositions are placed in water (e.g., by eliminating ions from the media for a certain amount of time), the injectable nanocomposite compositions can disperse (e.g., lose their solidity). In other words, when the injectable nanocomposite compositions were placed in water for a certain period of time, the injectable nanocomposite compositions "dissolved," losing their shape and rigidity, thus indicating that a birth control process using these types of biomaterials can be reversible. The graph of FIG. 2 quantifies the reversibility of some example injectable nanocomposite compositions in water (in terms of percentage of remaining mass over time). Additionally, the reversibility illustrated in FIG. 2 is in the absence of any flow. However, in the case of flow, the injectable nanocomposite compositions can be immediately reversed. The reversibility of the injectable nanocomposite compositions described herein can indicate a desired platform for occluding fallopian tubes, providing a reversible birth control option.

Figure 3A:
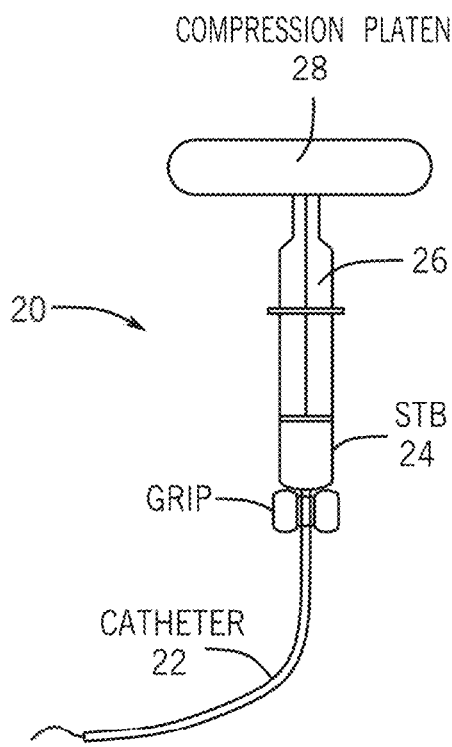
FIGS. 3A-3L illustrate results of mechanical testing of various nanocomposite compositions, where

Additionally mechanical testing of various nanocomposite compositions (L6, L6P1, L6P3, L6P5) was performed, as shown in FIGS. 3A-3L. More specifically, FIG. 3A illustrates a schematic of a setup 20 for measuring the injection force of the injectable nanocomposite composition 24, using a standard medical catheter 22 (e.g., 5 Fr). The injectable nanocomposite composition 24 is loaded into a syringe 26 (e.g., a 3 mL syringe), where the catheter 22 is attached to an end of the syringe 26. A compression plate 28 is then attached to a surface of a plunger of the syringe 26. Using this setup 20, injection forces of nanocomposite compositions 24 can be measured.

Figure 3B:
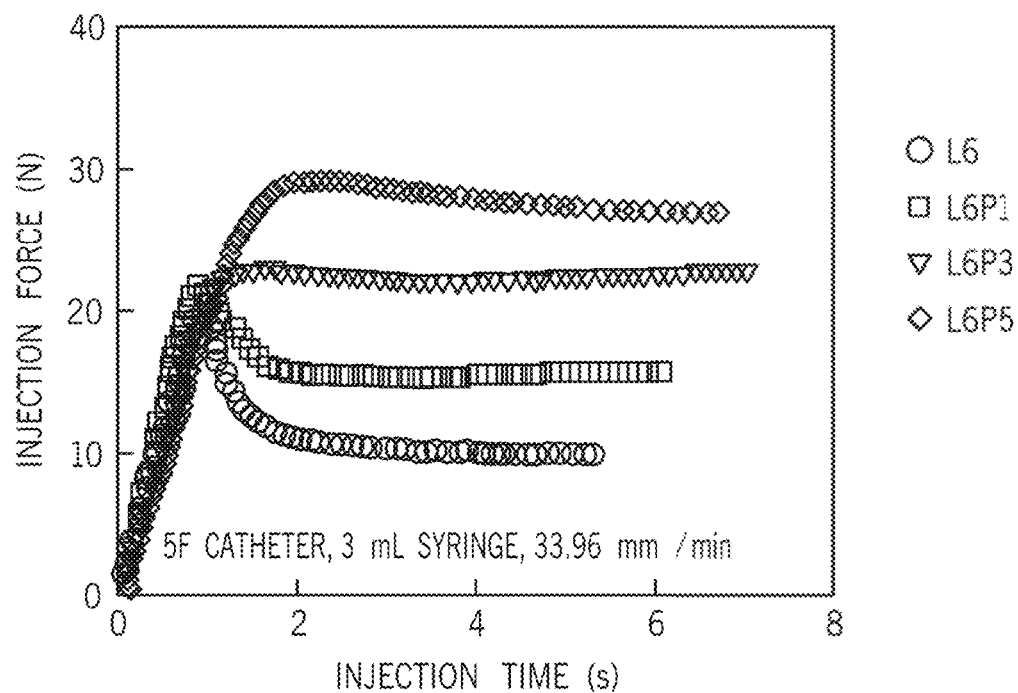

FIG. 3B illustrates injection forces (in Newtons, N) over time (in seconds, s) for various compositions using the setup of FIG. 3A. That is, the tested injectable nanocomposite composition was loaded in a 3 mL syringe and injected through a 5 Fr catheter (having a length of 65 cm) at a constant rate (33.96 millimeters per minute). The data collected and shown in FIG. 3B was measured using an Instron testing system. As shown in FIG. 3B, an increase in PEO concentration also can increase the injection force.

Figure 3C:
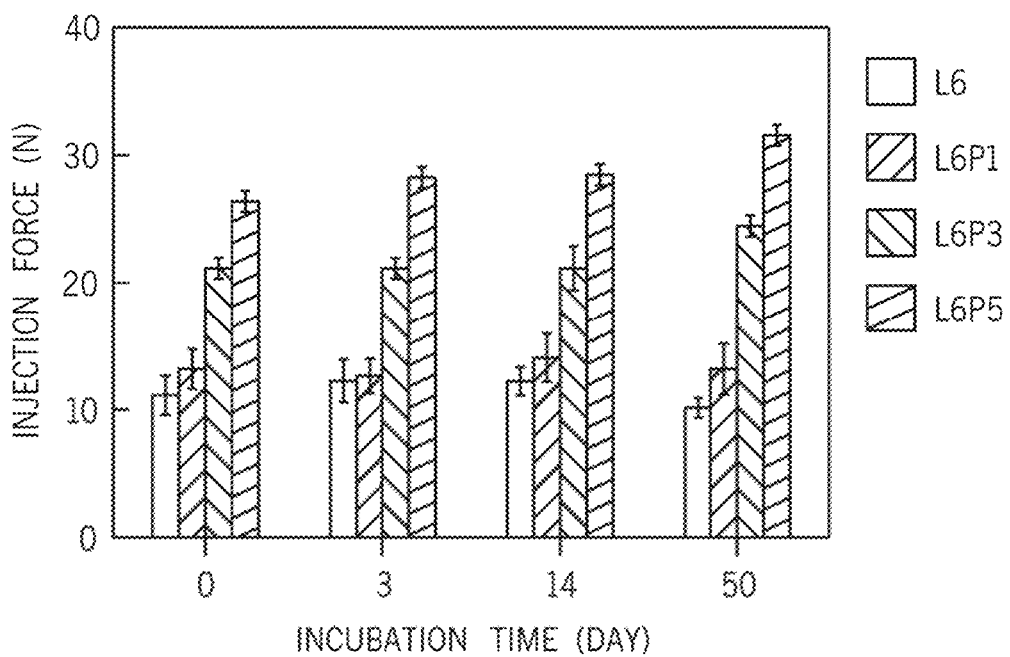

FIG. 3C illustrates injection forces of an injectable nanocomposite composition taken at different time intervals. For example, various injectable nanocomposite compositions were incubated at room temperature for a fixed duration (e.g., 0, 3, 14, and 50 days). At the end of the fixed duration, the specific injectable nanocomposite composition was tested using the setup of FIG. 3A. The injection force at increased injection times was collected (e.g., per the example of FIG. 3B) and graphed in FIG. 3C. As shown in FIG. 3C, as the incubation time duration increased, the injection force remained constant, thus indicating that there may be a negligible change in material property over time of the injectable nanocomposite compositions. The results of this testing support the determination that injectable nanocomposite compositions can have an extended shelf life.

Figure 3D:
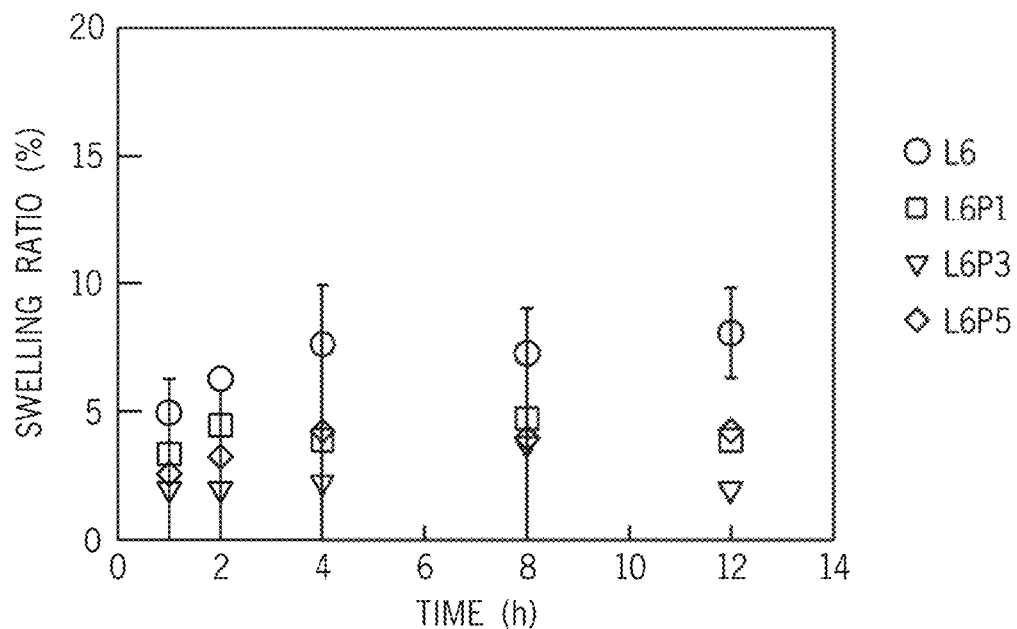
Figure 3E:
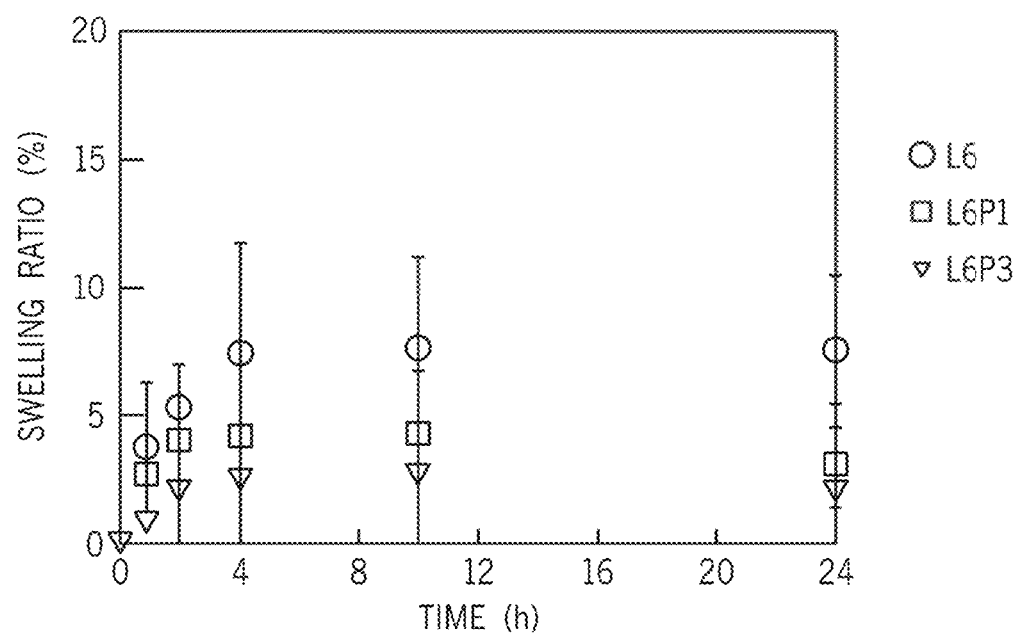

FIGS. 3D and 3E illustrate swelling ratios over time of injectable nanocomposite compositions in PBS and HTF, respectively. FIGS. 3D and 3E illustrate that an injectable nanocomposite composition absorbed <10% of the respective media during testing. Accordingly, these compositions can provide a sufficient platform for gradually absorbing tubal fluid in vivo, which can help prevent hydrosalpinx (that is, a condition in which a blocked fallopian tube fills with fluid).

Figure 3F:
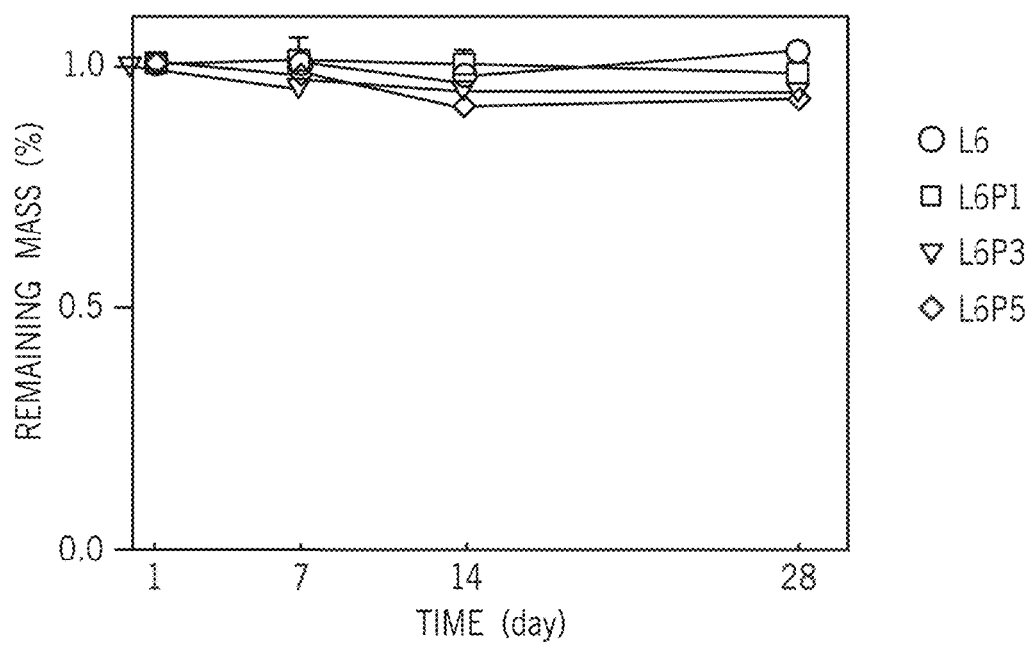

FIG. 3F illustrates percentage mass loss of injectable nanocomposite compositions over a specific duration of time, when incubated in PBS at 37° C. The results shown in FIG. 3F support that injectable nanocomposite compositions are generally not degraded for 28 days.

Figure 3G:
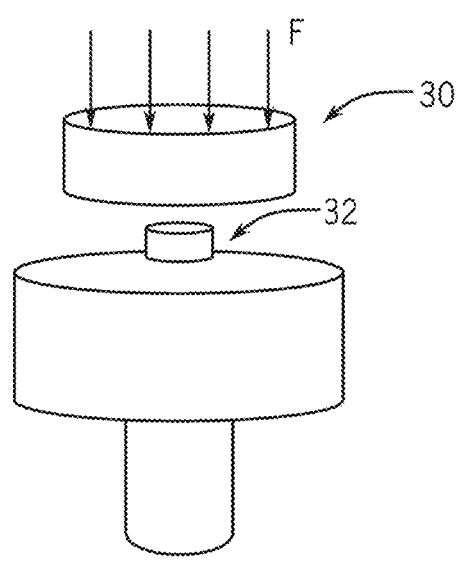
Figure 3H:
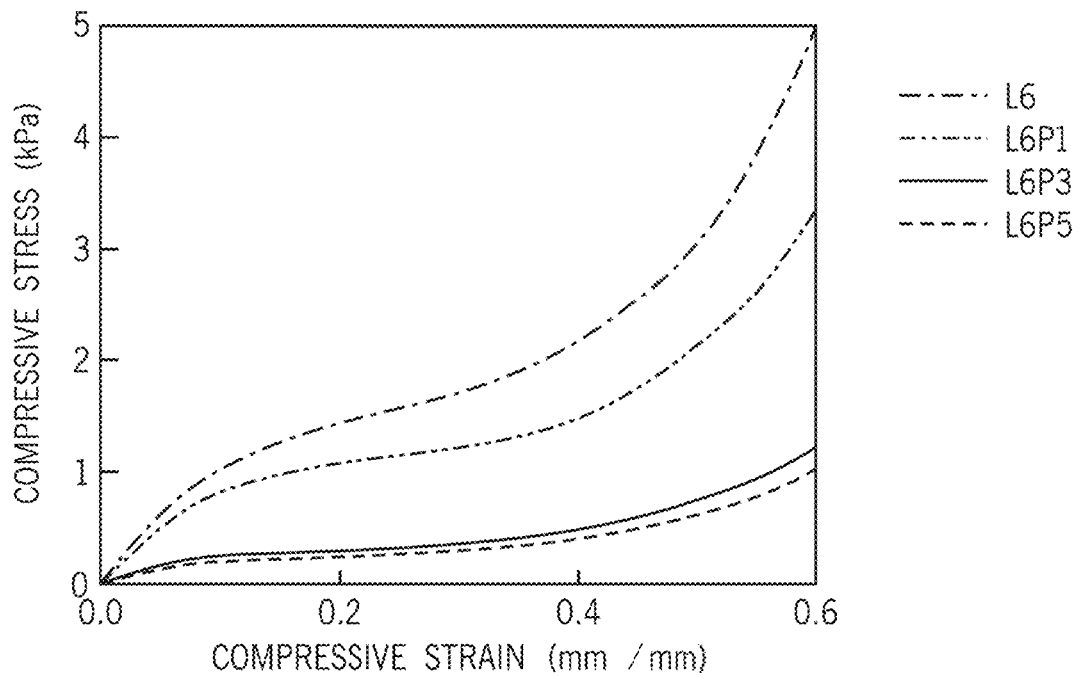
Figure 3I:
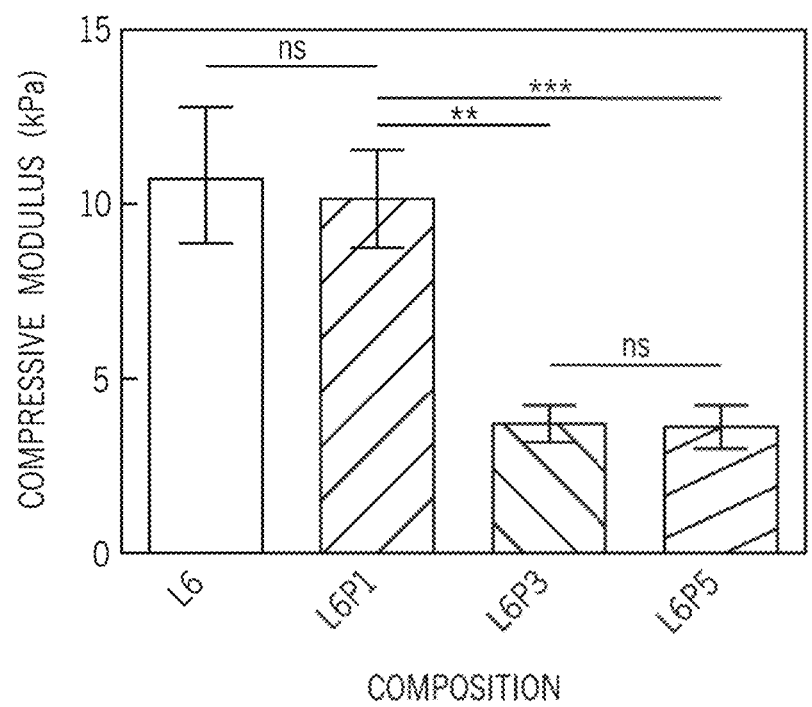

FIG. 3G shows an experimental procedure and system 30 to measure an injectable nanocomposite composition's compression modulus, an important representative of mechanical endurance under stress. According to this procedure, each of the injectable nanocomposite compositions can be shaped as a disc 32 (diameter ~1.5 cm, height ~0.3 cm) and placed on the corresponding material testing system 30. FIGS. 3H and 3I illustrate graphs of results using this procedure and setup.

More specifically, FIG. 3H illustrates compressive strain-stress for various injectable nanocomposite compositions (that is, compressive stress in kPa versus compression strain in mm/mm). Some of the injectable nanocomposite compositions (e.g., L=6%, P=0-5%, shown in FIG. 3H), showed no breakage. FIG. 3I illustrates compressive moduli (in kPa) of various injectable nanocomposite compositions. As shown in FIG. 3I, as PEO reaches ≥3%, the compressive modulus decreases, indicating a decrease in the mechanical properties of such compositions.

Figure 3J:
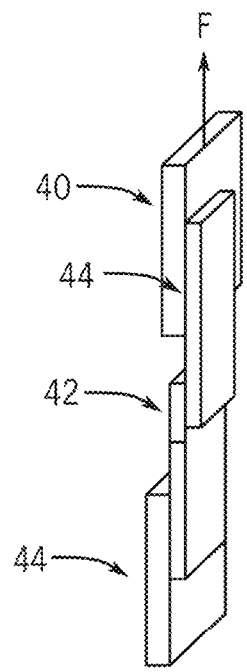
Figure 3K:
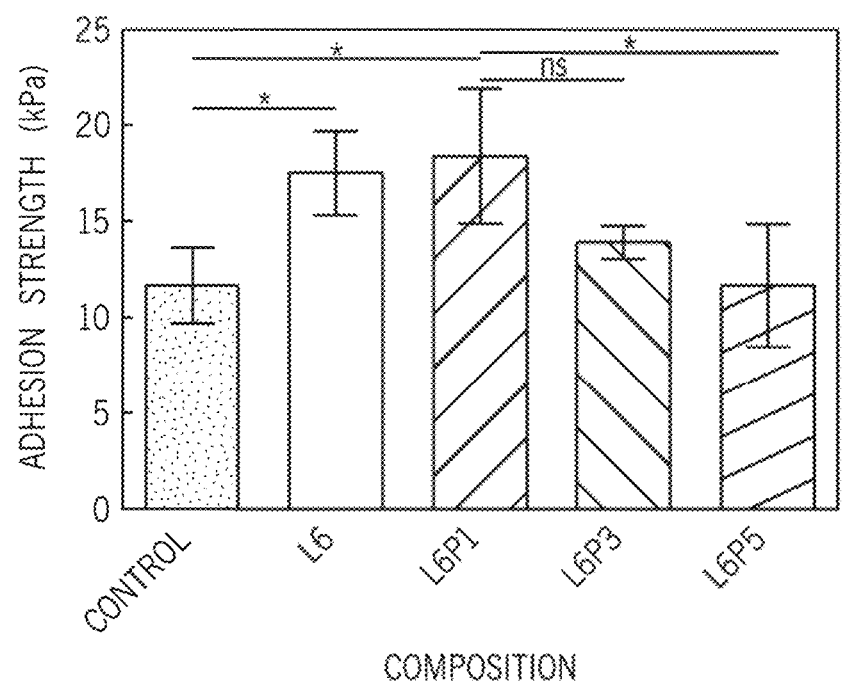
Figure 3L:
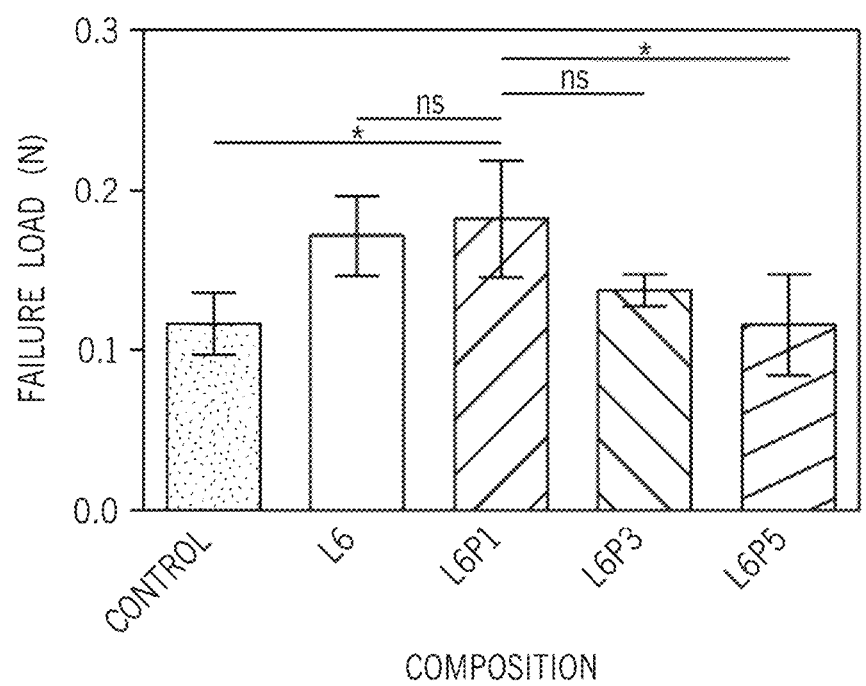

FIG. 3J shows a system setup 40 for conducting a lap shear analysis, which measures the adhesion strength of a 1 cm-by-1 cm area of an injectable nanocomposite composition 42, sandwiched between, for example, two pieces of uterine horn 44. FIGS. 3K and 3L illustrate graphical results of tests using the system 40 of FIG. 3J.

More specifically, FIG. 3K illustrates adhesion strength (in kPa) of various compositions using the system 40 of FIG. 3J, and obtained from a linear fit of each of the compressive stress-strain curves at a strain <10%. FIG. 3L shows the load at which the two tissue pieces (e.g., the two pieces of uterine horns) detach, thus defining a failure load (in N). As illustrated in FIG. 3L, an injectable nanocomposite composition (e.g., the "L6P1" composition) provides a sticky hydrogel, having the greatest failure load.

Figures 4A, 4B:
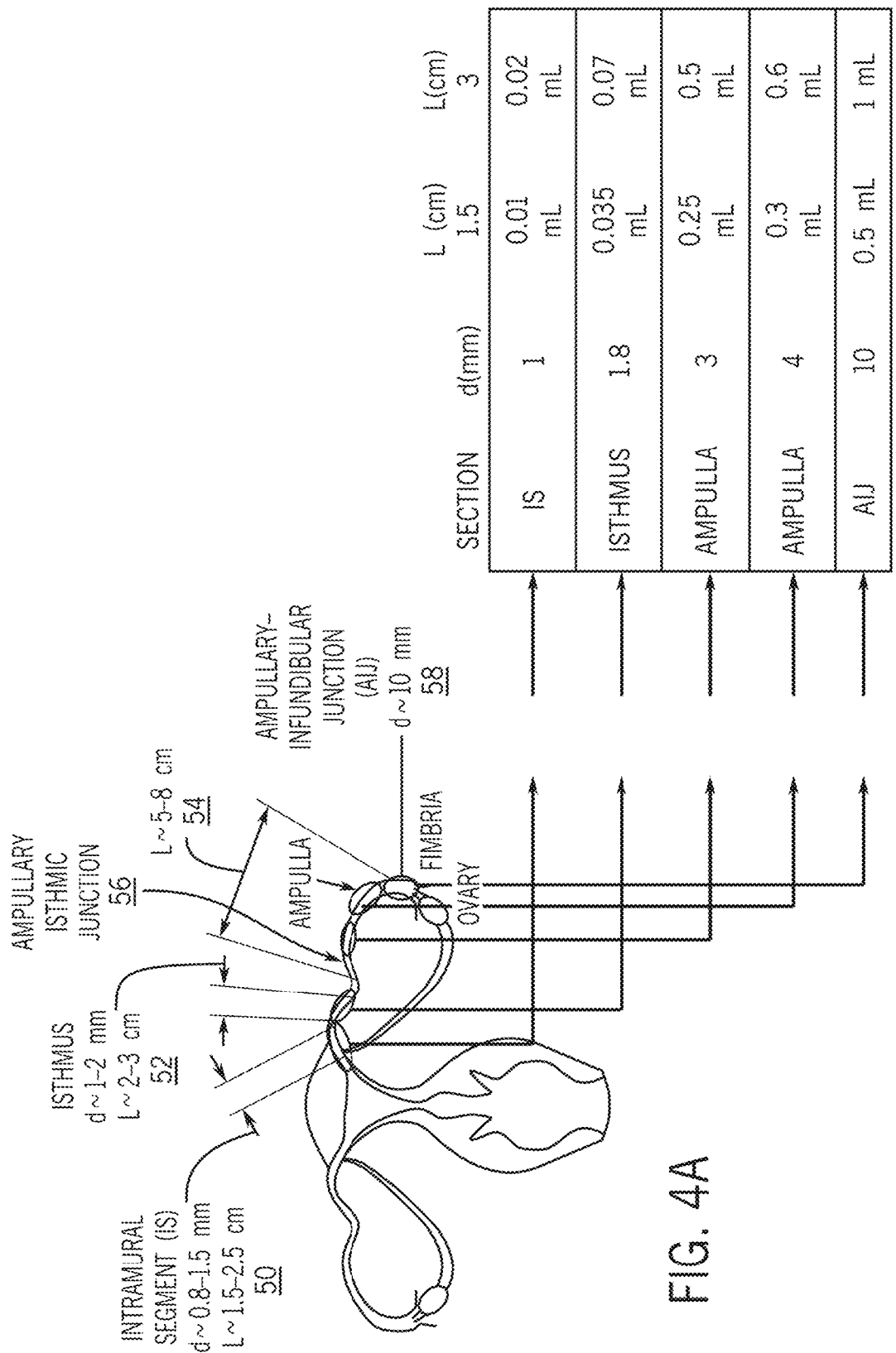
FIGS. 4A-4D illustrate a setup and tests of various nanocomposite compositions injected into tubes that resemble various structures of a fallopian tube, where

FIGS. 4A-4D show the capability of an injectable nanocomposite composition in occluding tubes that resemble different regions of a fallopian tube. For example, FIG. 4A shows an illustration of the female reproductive system anatomy, and specifically shows the size of four separate regions of the fallopian tube: the intramural segment ("IS") 50, the isthmus 52, the ampulla 54 (including the ampullary isthmic junction 56), and the ampullary-infundibular junction ("AIJ") 58. The IS generally has a diameter of about 0.8-1.5 millimeters (mm) and a length of about 1.5-2.5 cm. The isthmus generally has a diameter of about 1-2 mm and a length of about 2-3 cm. The ampulla generally has a length of about 5-8 centimeters. The AIJ generally has a diameter of about 10 mm.

FIG. 4B illustrates a list of sample "tubes" mimicking anatomical characteristics (i.e., diameter) of each section of the fallopian tubes. More specifically, according to an example experiment, each of the tubes can be used to evaluate the occlusion potential of nanocomposite compositions while exposed to air, water, or PBS. Each tube (e.g., having an occlusion length L=1.5 cm or 3 cm) can be filled with the nanocomposite composition, using the amount specified in the table. In FIG. 4B, the first column of the table provides the section type, the second column provides the tube diameter (in mm) mimicking that specific section, the third column provides the amount nanocomposite (in mL) for a 1.5-centimeter occlusion length, and the fourth column provides the amount nanocomposite (in mL) for a 3-centimeter occlusion length. In this experiment, the tubes were made of tygon.

Figure 4C:
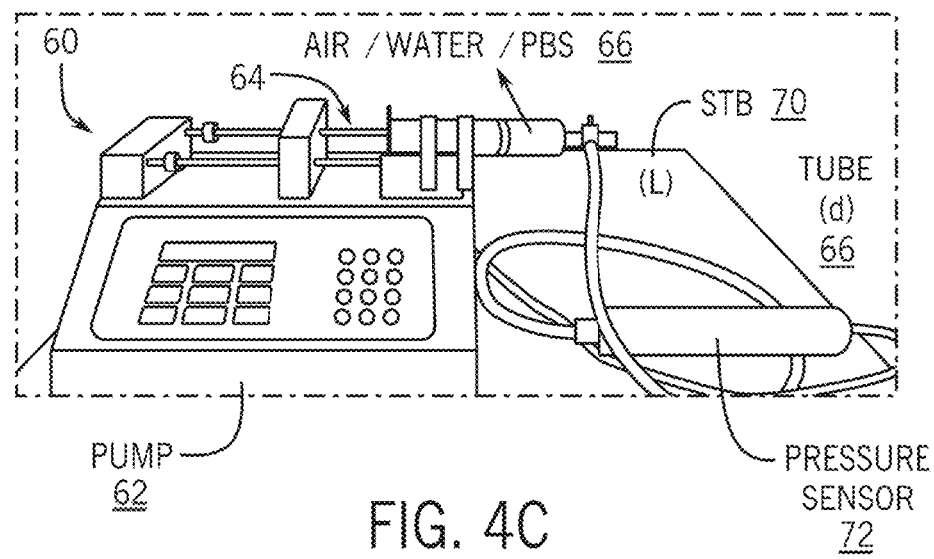
Figure 4D:
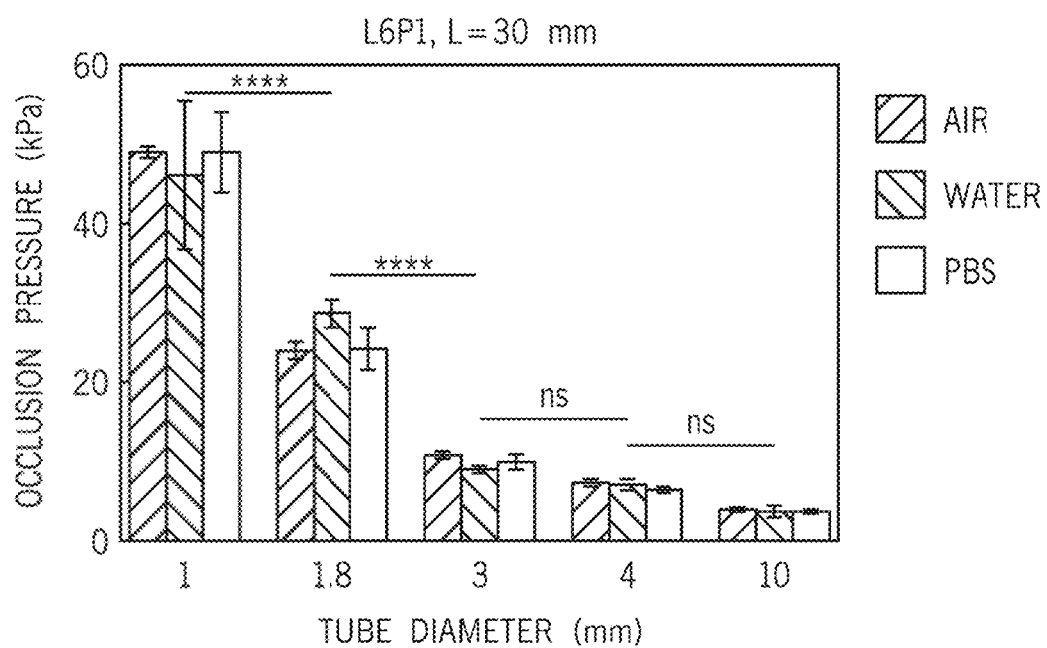

FIG. 4C shows an experimental setup 60 used to measure the maximum pressure ("occlusion pressure") that certain nanocomposite compositions can withstand within each of the various tubes described above with respect to FIG. 4B. The setup 60 includes a pump 62 coupled to a syringe 64 filled with a material 66 (air, water, or PBS). The syringe 64 is coupled to a sample tube 68 having a diameter d, containing a length L of nanocomposite 70. A pressure sensor 72 is further coupled to the syringe 64. The results of this setup 60 are illustrated in FIG. 4D. More specifically, FIG. 4D shows occlusion pressure (in kPa) of tubes having different diameters when blocked using the L6P1 nanocomposite composition (occlusion length of approximately 30 mm) while exposed to air, water, or PBS.

Figure 5:
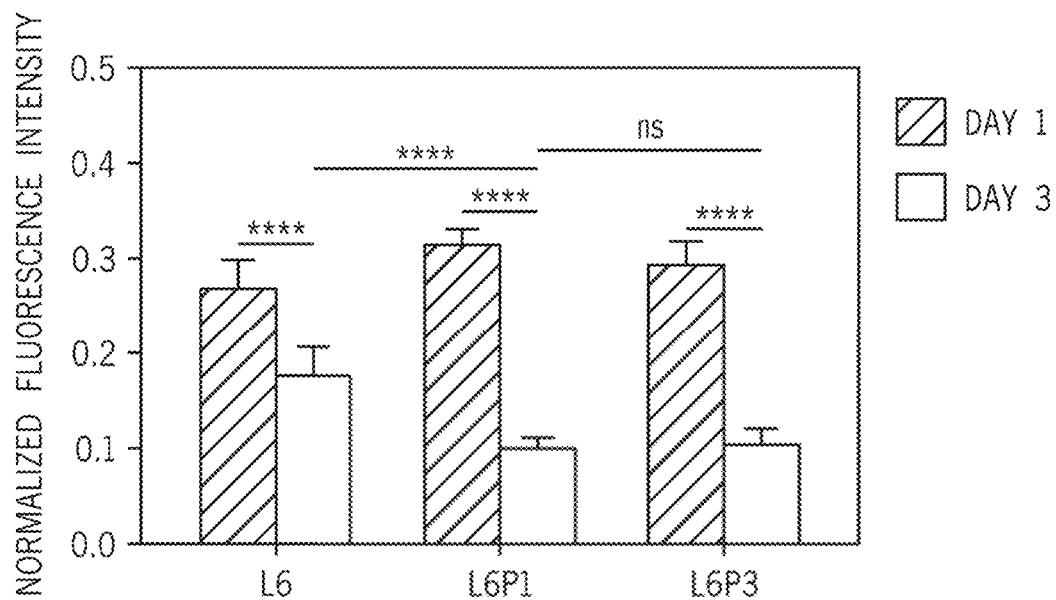
FIG. 5 illustrates test results demonstrating how various nanocomposite compositions provide non-adhesive substrates for cells and, more specifically, a graph of composition versus normalized fluorescence intensity.

In accordance with FIG. 5, additional testing was performed to show how nanocomposite compositions can provide non-adhesive substrates for cells within a model cell line (e.g., NIH/3T3 fibroblasts). This can be essential in preventing cell infiltration, and thus preventing fibrosis. More specifically, in order for the birth control to be reversible using the materials described herein, the nanocomposite composition should not cause fibrosis to occur. Thus, in some embodiments, the nanocomposite compositions may substantially inhibit cell infiltration.

For example, bright field optical images of NIH/3T3 fibroblasts interacting with various 2-dimensional nanocomposite substrates (L6, L6P1, and L6P3) and a control substrate (plastic) were collected. In the images, the fibroblasts were shown to spread over and adhere to the control substrate, whereas the cells experienced impaired spreading and adhesion on the nanocomposite compositions (e.g., on the L6 composition). Some nanocomposite compositions (e.g., the L6P1 and L6P3 compositions) completely prevented cell spreading, and thus provide a poor substrate for cells. Furthermore, images of live/dead staining of cells adhered to the nanocomposite compositions were also collected. According to these images, the adhesion and proliferation of cells on the control substrate is evident. However, the number of cells that remain attached to the nanocomposite compositions are negligible.

FIG. 5 illustrates the metabolic activity of cells on these nanocomposite compositions, quantified using PrestoBlue cell viability reagent. More specifically, FIG. 5 illustrates normalized fluorescence intensity for various compositions after one day and three days. The results of FIG. 5 show a reduced metabolic activity of cells on the nanocomposite compositions as a result of cell detachment and a lack of strong cell adhesion/spreading.

The above discussion illustrates the physical, mechanical, barrier, and biological properties of nanocomposite compositions in accordance with some applications and their viability for use as a biomaterial for reversible birth control. In some embodiments, the nanocomposite compositions can be optimized to yield an injectable hydrogel with sufficient stability and strength in certain physiological conditions and that also may be able to disperse when desired. In some embodiments, nanocomposite compositions can further have a long shelf life with minimal degradation over time, be able to gradually absorb fluids, and prevent fibrosis.

Figure 6:
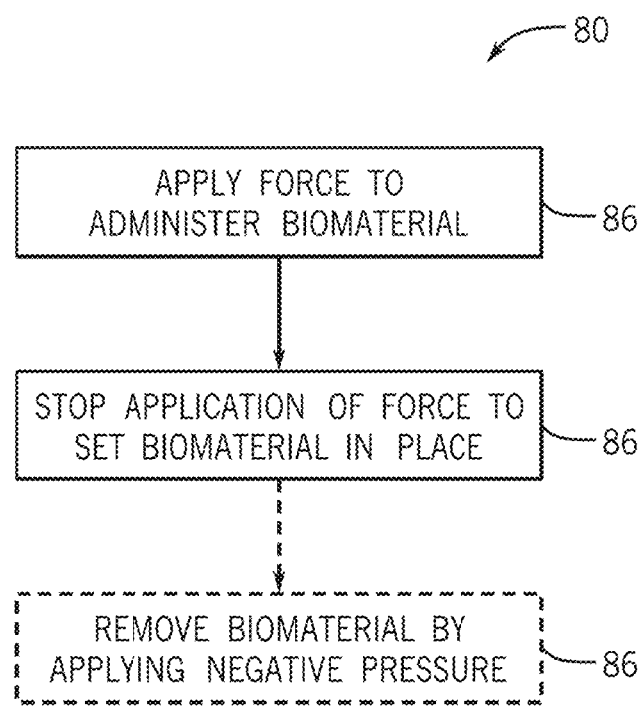
FIG. 6 illustrates method for providing reversible birth control.

In light of the above discussion, FIG. 6 illustrates a method 80 for reversible birth control according to some embodiments. Generally, the method 80 includes administering a biomaterial into one or both fallopian tubes of a subject, where the biomaterial is a shear-thinning nanocomposite in accordance with the above discussion. That is, the method 80 includes applying adequate force to administer the shear-thinning nanocomposite into a subject's fallopian tubes (step 82), and stopping application of such forces once the nanocomposite is inserted in order to set the nanocomposite in place (step 84). Optionally, once birth control is no longer desired, the method further includes removing the nanocomposite by applying a negative pressure (step 86).

More specifically, at step 82, using adequate force, a therapeutically effective amount of shear-thinning nanocomposite can be injected into each fallopian tube of a subject. Pressure is applied to the shear-thinning nanocomposite to cause it to flow, in a gel-like state, into the fallopian tube. With reference to FIGS. 7A-7D (illustrating the method performed on a pig uterus) this step may be performed by delivering a standard endovascular catheter 88 and/or glide wire 90 through the subject's intrauterine cavity until a tip 92 of the catheter 88 is positioned at a respective fallopian tube 94 (e.g., at the uterine horn).

In some embodiments, the catheter 88 may be pre-loaded with the composition 96, while in other embodiments, the catheter 88 may be loaded after placement at the fallopian tube, for example, via a syringe. Additionally, in some embodiments, this step (or any other steps of the present method 80) can be performed using imaging guidance, such as CT, x-ray, ultrasound, or other suitable imaging techniques, as further described below. That is, the fallopian tube and/or surrounding anatomy may be imaged while administering the composition 96 to guide the administration. For example, in one application, this step can be performed under real-time fluoroscopy guidance (e.g., in an interventional radiology suite). However, in other applications, the method 80 may be performed without image guidance.

Figure 7A:
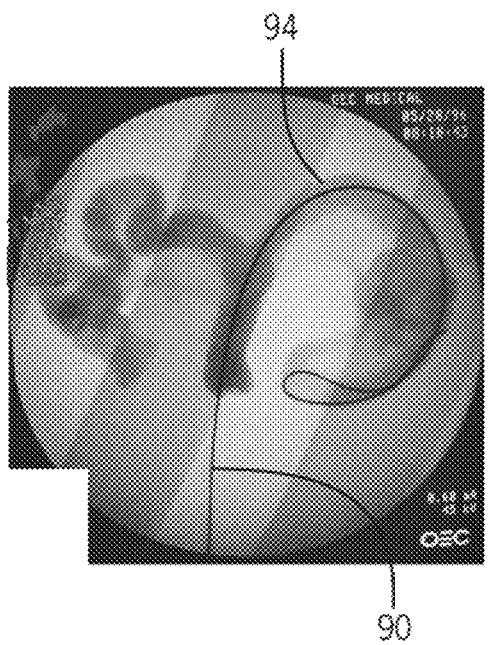
Figure 7A:
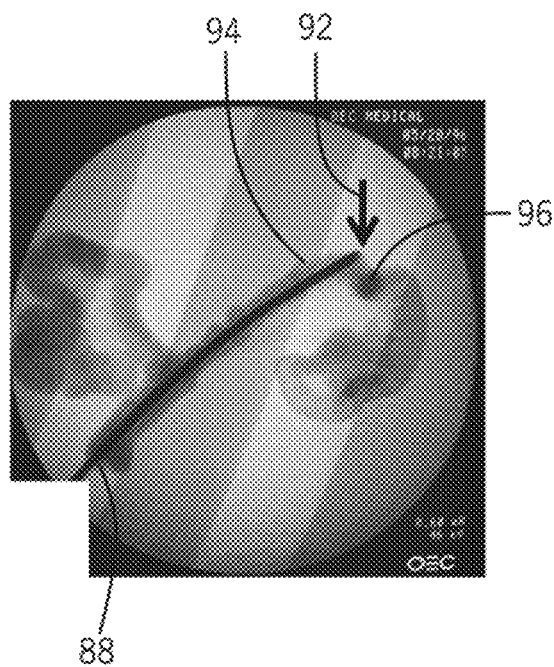
Figure 7A:
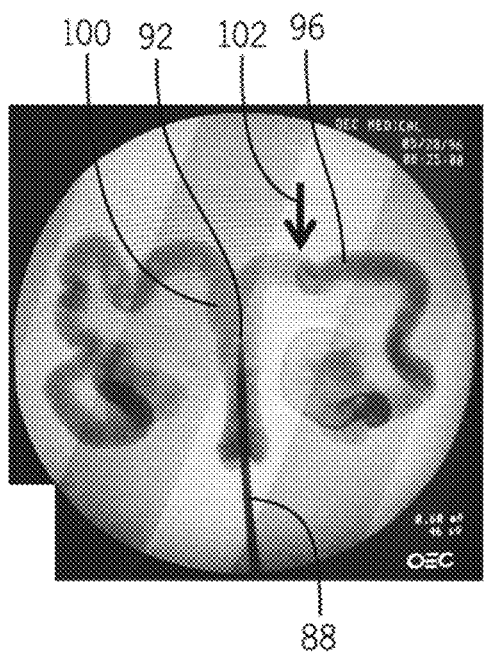
Figure 7A:
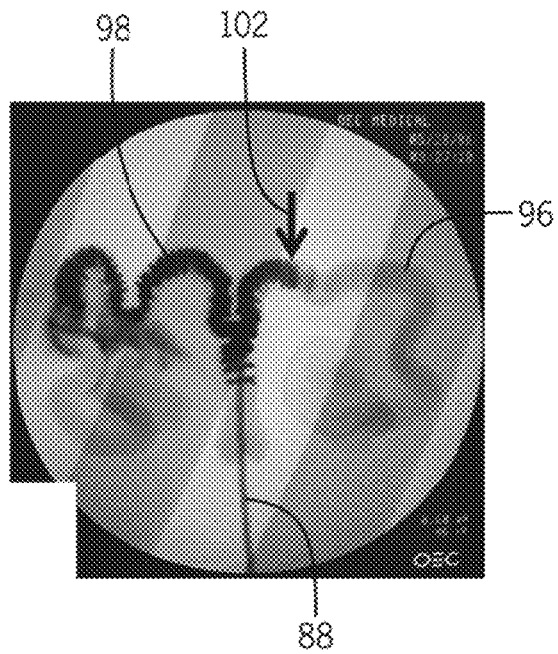

By way of example, FIG. 7A illustrates the glide wire 90 being directed through a subject's intrauterine cavity into a fallopian tube 94. In this example, a 0.035 inch glide wire is used. Once the glide wire 90 is placed in the desired location, a catheter 88 is placed coaxially over the wire 90 so that the catheter 88 can then travel along the glide wire 90. Once the catheter 88 travels through the intrauterine cavity to its final location (e.g., reaching the uterine horn), the glide wire 90 can be removed and the catheter 88 can be connected to a syringe (not shown) containing the nanocomposite biomaterial (i.e., composition 96). FIG. 7B illustrates the biomaterial 96 being infused, via compression of the syringe. Compressing the syringe can provide the necessary application pressure to change the nanocomposite biomaterial from a solid to a liquid or gel-like material that flows (i.e., due its shear-thinning material property). In the liquid state, the nanocomposite biomaterial completely fills the fallopian tube cavity.

At step 84, once the application forces are no longer applied, the composition 96 is set in place and the catheter 88 can be removed. More specifically, once pressure from the syringe is no longer applied, the composition 96 can change from a gel-like state to a solid state over a time period (e.g., an equilibrium time period). Once in the solid state, the composition 96 creates an impenetrable cast through the fallopian tube 94, thus blocking sperm mobility through the fallopian tube 94. Additionally, as the nanocomposite 96 can conform to the shape of the fallopian tube 94 while in the gel-like state, and then keep that shape while in the solid state, the nanocomposite 96 is not affected by different orientations or sizes of the subject's reproductive organs.

Alternatively, in some applications, a needle may be used in place of the catheter 88. In one specific example, CT, US, or MRI guidance can be used to access a fallopian tube in a percutaneous manner with a needle. Once accessed, the nanocomposite can be delivered directly to the fallopian tube by applying pressure (e.g., via a needle plunger).

Accordingly, after removal of the expulsion force from the syringe or needle, the nanocomposite biomaterial 96 solidifies, and occludes the fallopian tube 94. Referring back to the example of FIGS. 7A-7D, to ensure that the fallopian tube 94 is sufficiently occluded, a contrasting agent 98 can be forcefully injected into the uterine cavity 100, for example, via a syringe connected to a catheter 90. FIG. 7C illustrates the procedure just before injection of the contrasting agent, where the tip 92 of the catheter 88 rests in the uterine cavity 100, and the solidified composition 96 provides a blockage 102. FIG. 7D illustrates injection of the contrast agent 98 (e.g., with high force exceeding 100 Newtons), validating the success of the blockage 102. As illustrated in FIG. 7D, the injected contrast agent 98 only flows through the unoccluded passage up to the biomaterial 96, then reverses direction and fills the contralateral fallopian tube. As such, the blockage 102 successfully prevents any contrast agent from leaking into the occluded fallopian tube 96. Thus, because no contrast agent 98 is seen in the occluded fallopian tube 96, this test validates that the fallopian tube 98 is completely occluded by the biomaterial 96 and capable of withstanding high pressure forces.

Figure 8:
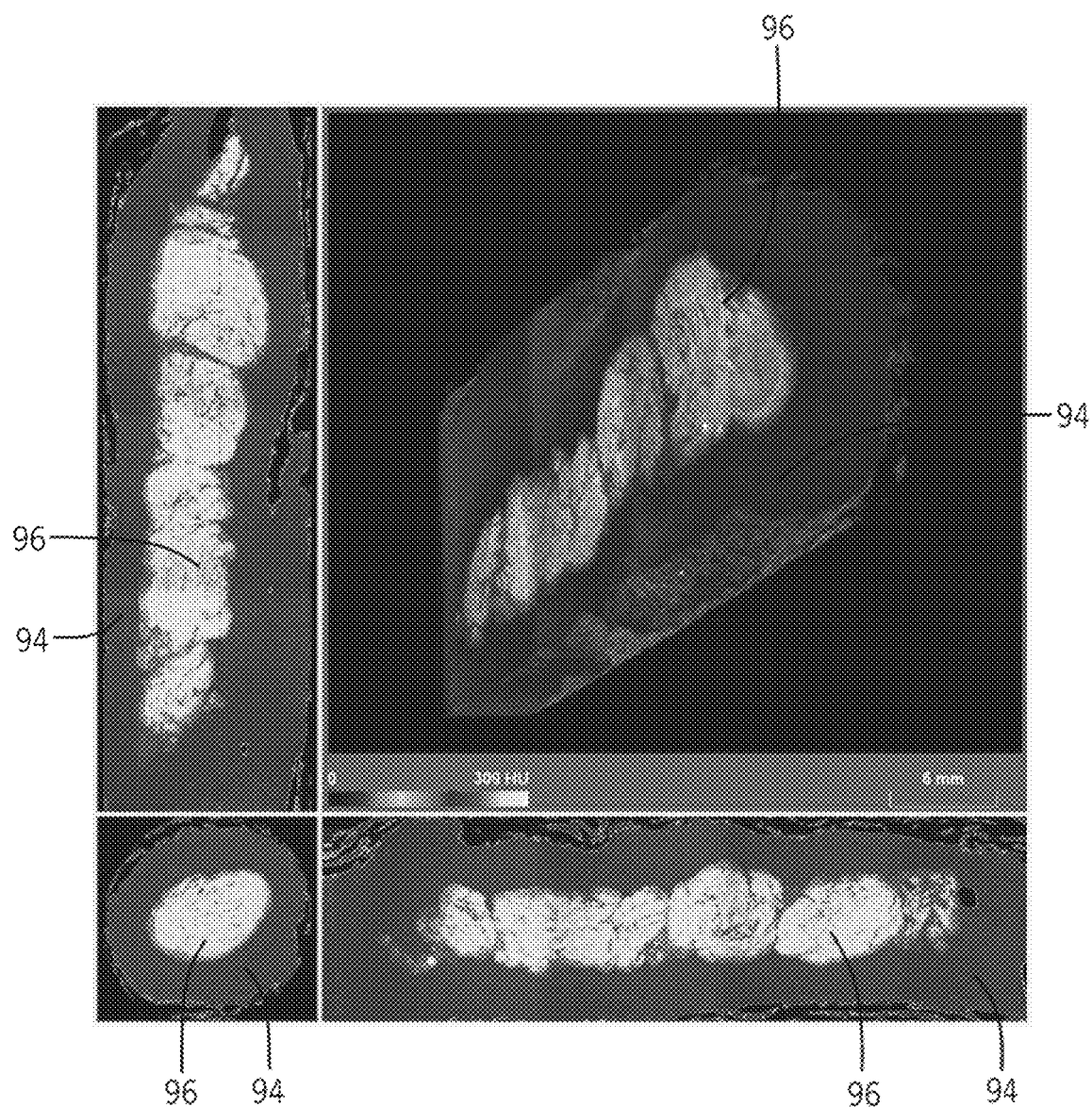
FIG. 8 illustrates a series of CT images showing a fallopian tube occluded by a nancomposite composition in accordance with aspects of the disclosure.
Figure 9:
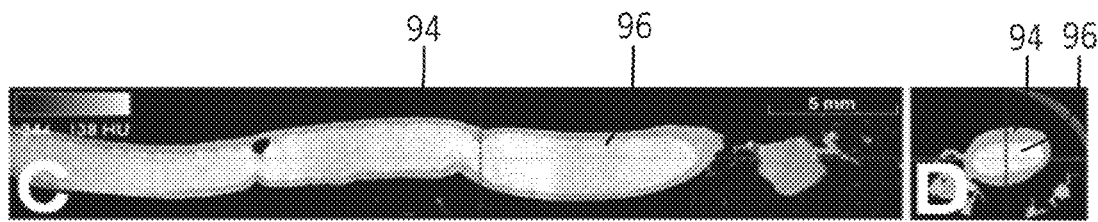
FIG. 9 illustrates another series of CT images showing a fallopian tube occluded by a nancomposite composition in accordance with aspects of the disclosure.

Furthermore, FIGS. 8 and 9 illustrate CT images of a fallopian tube 94 occluded by the composition 96 in accordance with the above method. As shown in FIGS. 8 and 9, the composition 96 tightly hugs the walls of the fallopian tube 94. Accordingly, the composition 96 can prevent sperm from traveling through the fallopian tube 94 to reach or fertilize an egg and, as a result, can provide effective birth control. In some embodiments, once in the solid state, the pressure required to induce composition displacement (i.e., to cause the composition 96 to change back to gel-like state) exceeds, for example, up to 400 mmHg. Thus, the composition 96 can remain in place and withstand external compression from adjacent organs, fluids, or palpitation.

In some applications, steps of the method 80 can be applied to a hysterosalpingogram procedure. More specifically, during a typical hysterosalpingogram, a first glide wire is guided into the vaginal canal, past the cervix, through the uterus, and into a first fallopian tube. A second glide wire, using the same method, can be placed within a second fallopian tube. A catheter is placed coaxially around the first glide wire and is moved into the first fallopian tube. Contrast is then ejected into the fallopian tube, in order to aid in imaging any scar tissue within the first fallopian tube. Contrast can also be ejected into the second fallopian tube using the same method as discussed above with respect to the first fallopian tube.

Accordingly, a typical hysterosalpingogram procedure can be modified using components of method 80. For example, rather than or just before injecting the contrast agent, the composition 96 can be injected, as discussed above with reference to FIGS. 7A-7B. After the composition 96 has been placed within the first and/or second fallopian tube, a contrast agent can be ejected into the uterus to ensure that the fallopian tubes have been occluded properly. This slight modification is advantageous to the current field, as doctors trained in hysterosalpingograms will be able to quickly implement the proposed adjusted procedure.

Referring now to step 86 of the method of FIG. 6, once birth control is no longer desired, the composition 96 may be removed from the fallopian tubes 94. In one embodiment, a catheter 88 can be inserted into the uterine cavity and positioned at a respective fallopian tube 94 so that the catheter tip 92 is adjacent the composition 96. Once positioned, negative pressure can be applied through the catheter 88 to aspirate the composition 96, thus removing it from the fallopian tube 94. More specifically, the applied negative pressure causes the composition 96 to revert back to the gel-like state, permitting the composition 96 to flow from the fallopian tube 94 back into the catheter 88.

In some embodiments, rather than injecting the composition 96 into a first and/or second fallopian tube 94, as described above, the composition 96 can instead be injected into the uterus. Once the composition 96 hardens (e.g., by the removal of the injection pressure), a barrier is formed that isolates the uterus from the vagina by blocking the pathway through the cervix. This barrier thus prevents sperm from traveling into the uterus, effectively preventing pregnancy. Furthermore, this barrier within the uterus would also prevent ovulation.

Additionally, during menstruation, the composition 96 within the uterus can change from a solid back to a gel-like state due to the shear-thinning material properties of the composition 96. More specifically, during menstruation, the uterus contracts, aiding in the expulsion of the uterine lining out of the body. This contraction of the uterus during menstruation can also provide the forces necessary to change the composition 96 from a solid state to a flow-able gel-like state, allowing the composition 96 to expel from the body. In other words, the composition 96 would expel itself like natural menstruation.

Furthermore, although the method 80 has been described with regard to female anatomy for birth control (e.g., placement within the fallopian tubes and/or uterus), another aspect of the invention relates to applying the method 80 for male birth control. For example, rather than occluding the fallopian tubes, the composition 96 can occlude the vas deferens in a male subject. A glide wire (e.g., glide wire 90) can be inserted through the urethral opening, traveling through a seminal vesicle and into the vas deferens. Similar to that discussed above, a catheter (e.g., catheter 88) can be placed coaxially around the glide wire, and can travel along the glide wire from the penile urethra into ejaculatory duct, then into the ampulla of ductus deferens and into the vas deferens. Once the catheter 88 is placed into the vas deferens, the composition 96 can be ejected using a compressive force, through the catheter 88, thus activating the shear-thinning properties of the composition 96 and allowing the composition 96 to readily flow into the vas deferens. Upon removing the compressive force, the composition 96 solidifies and occludes the vas deferens. The catheter 88 is then removed, and this procedure can be repeated for the second vas deferens. In another approach, the vas deferens can be accessed using ultrasound guidance. For example, a 27-gauge needle can enter the lumen of the duct, where the composition 96 could then be injected. The composition 96 will create a cast of the duct, effectively preventing sperm transit. Once the vas deferens ducts are occluded, sperm cannot migrate through the seminal vesicles and into the urethra, thus effectively preventing sperm from reaching an ovum and preventing pregnancy.

Thus, the above method can act similar to a vasectomy (e.g., where the vas deferens is cut to prevent sperm from reaching semen and being expelled), but would be minimally invasive and reversible. For example, if the male decides to have children, the composition 96 can be removed via a similar procedure that placed the composition 96 into the vas deferens. That is, rather than the catheter 88 expelling the composition 96 and allowing it to flow into the vas deferens, a reverse pressure is applied to the catheter 88 allowing the composition 96 to flow back into the catheter 88. For example, access to the vas deferens is obtained from the penile urethra. Once the composition 96 is reached, suction is applied to the catheter 88 to aspirate the composition 96 until it is removed. Once the composition 96 is removed through the catheter 88, sperm may freely travel through the vas deferens, into the seminal vesicles, and into the urethra, thus re-enabling the ability for the male subject to fertilize an ovum.

Figure 10A:
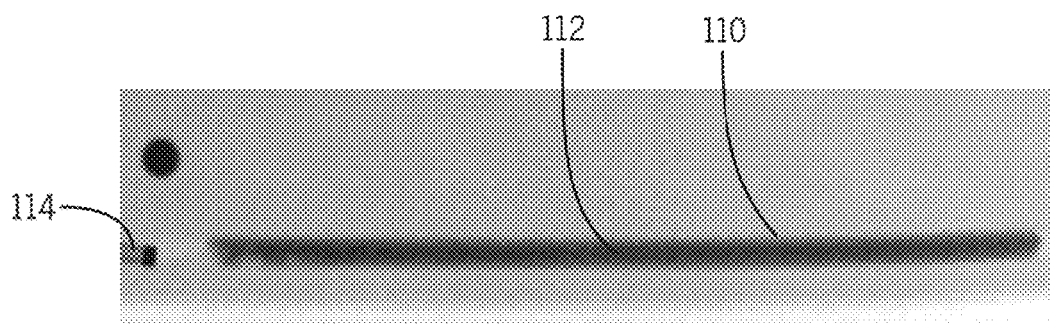
FIGS. 10A, 10B, 10C, and 10D illustrate a series of x-ray images of a biomaterial being aspirated from a sample tube mimicking a vas deferens.
Figure 10B:
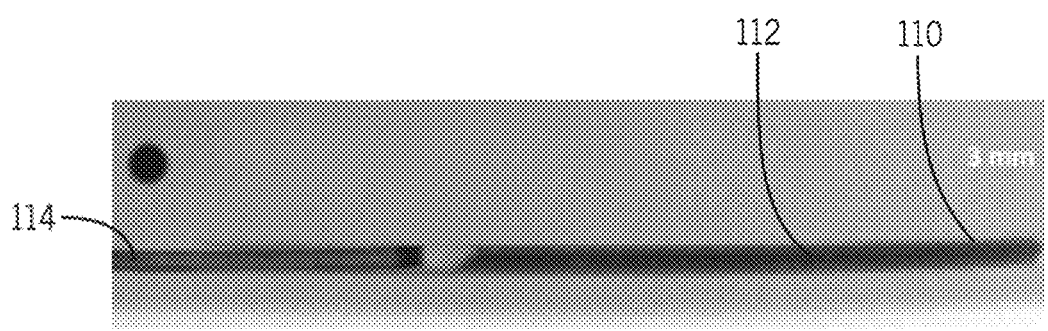
Figure 10C:
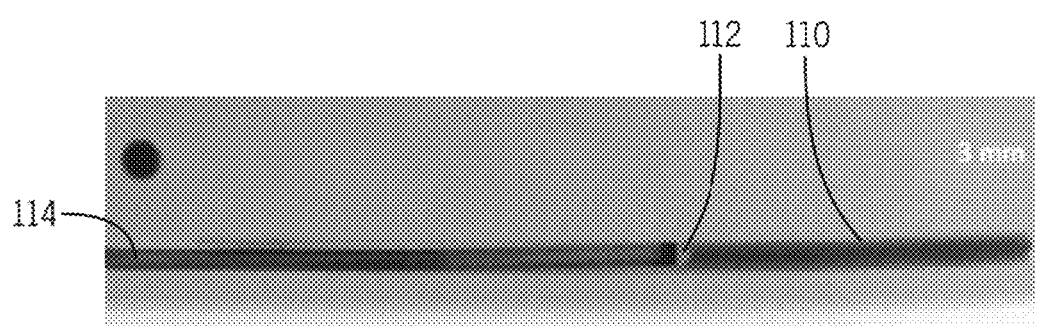
Figure 10D:
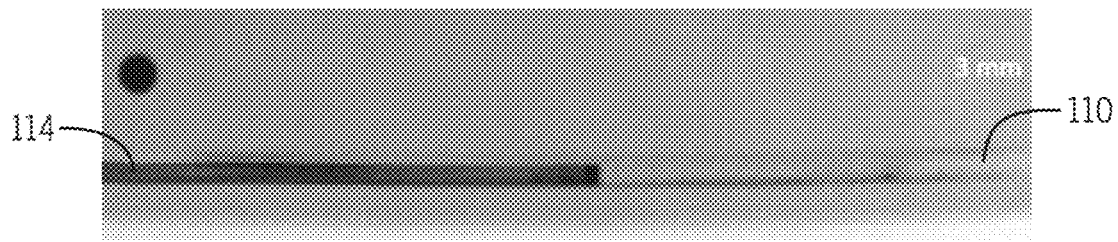

By way of example, FIGS. 10A-10D show a series of images illustrating complete retrieval of a nanocomposite composition from a sample tube mimicking the size of the vas deferens. More specifically, FIG. 10A illustrates an image of a 3D printed tube 110 (approximately 3 mm) containing a nanocomposite composition 112 in accordance with the above discussion. FIGS. 10B and 10C illustrate images of a syringe 114 being used to aspirate the composition 112 from the tube 110. Finally, FIG. 10D illustrates an image of the composition 112 completely removed from the tube 110 by the syringe 114. While the syringe 114 is used in the example shown and described herein, other mechanisms for applying negative pressure also be used in some applications such as, but not limited to, commercially available aspiration systems (e.g., a Penumbra Aspiration Catheter (Penumbra, Inc.)).

Accordingly, the above methods provide for reversible birth control using a shear-thinning nanocomposite administered to a subject's reproductive anatomy (e.g., fallopian tubes, uterus, or vas deferens). Once birth control is no longer desired, the composition can be completely removed from the subject. In other words, the composition can be retrieved after earlier occlusion, thereby re-permitting sperm mobility to the fallopian tubes immediately after removal.

In some embodiments, in addition or alternative to the above birth control methods, the compositions provided herein may be administered to one or more of a subject's reproductive organs (e.g., fallopian tubes, uterus, vagina, ovaries, vas deferens, etc.) in combination with an additional therapeutic agent for the treatment of a disease or disorder in the subject, such as, but not limited to, cancer, a tumor, an infection, an abscess, or a fistula. For example, the shear-thinning compositions provided herein may be used as a carrier of therapeutic agents such as, but not limited to, chemotherapy agents, antimicrobial agents, adhesive agents, anti-inflammatory agents, regenerative agents, hemostatic agents, steroids, anti-allergic agents, anesthetics, immunosuppressants, and anti-fungal agents. Additionally, in some embodiments, along with the ability to occlude a passage and prevent pregnancy, the composition can include agents that further mitigate the risk of pregnancy and/or provide a reduction in symptoms related to menstruation. For example, the composition can be loaded with hormones (e.g., progesterone, estrogen, etc.) that are controllably released. The hormones are then absorbed into the subject and can physiologically affect the subject locally and/or systemically.

As such, in some applications, a therapeutically effective amount of nanocomposite, including a therapeutic agent, can be administered, via a subject's intrauterine cavity, to a target reproductive organ to deliver therapy or treatment for a time period and then removed (again, via the subject's intrauterine cavity) after the time period has expired. For example, according to one application, a therapeutically effective amount of nanocomposite, including a chemotherapy agent, can be injected into a subject's intrauterine cavity to provide sustained delivery of chemotherapy to the subject's uterus. In another example, a therapeutically effective amount of nanocomposite, including a chemotherapy agent, can be injected into the fallopian tubes as a therapeutic agent for cancers in the reproductive organs or in the intraperitoneal space. In yet another example, a therapeutically effective amount of nanocomposite, including a therapeutic agent, can be injected into the uterus to deliver the agent to the uterine mucosa (and the nanocomposite can naturally wash out during menstruation). In accordance with these methods, the nanocomposite may be administered to a target reproductive organ generally (such as the vagina, the uterus, the fallopian tubes, or the ovaries) or any particular portion of or growth within or adjacent to such reproductive organs. Such methods may also be applicable to a male subject's reproductive anatomy.

Any of the above-described methods may be carried out using a kit comprising one or more components of a shear-thinning composition, one or more catheters, one or more syringes, and/or one or more therapeutic agents. For example, in some embodiments, such a kit comprises a pharmaceutically acceptable amount of a shear-thinning composition preloaded into one or more of the catheters.

In accordance with the above description, embodiments of the invention provide a method of reversible birth control by occluding fallopian tubes with a biomaterial that is biocompatible, non-toxic, and conformable to the subject's anatomy. Additionally, or alternatively, embodiments of the invention provide a method for administering a therapeutic agent to a subject's reproductive organs using such a biomaterial. The biomaterial, a shear-thinning nanocomposite, is capable of being administered via an intrauterine catheter by applying pressure, causing it to change from a solid state to a gel-like state. Once pressure application is removed, the biomaterial returns to a solid state and can withstand external compression from adjacent organs, fluids, or palpitation. The biomaterial can be applied to and removed from the reproductive organs via a catheter inserted through the intrauterine cavity and, as a result, the methods herein are minimally invasive and do not require extensive surgery for biomaterial insertion or removal.

Figure 11:
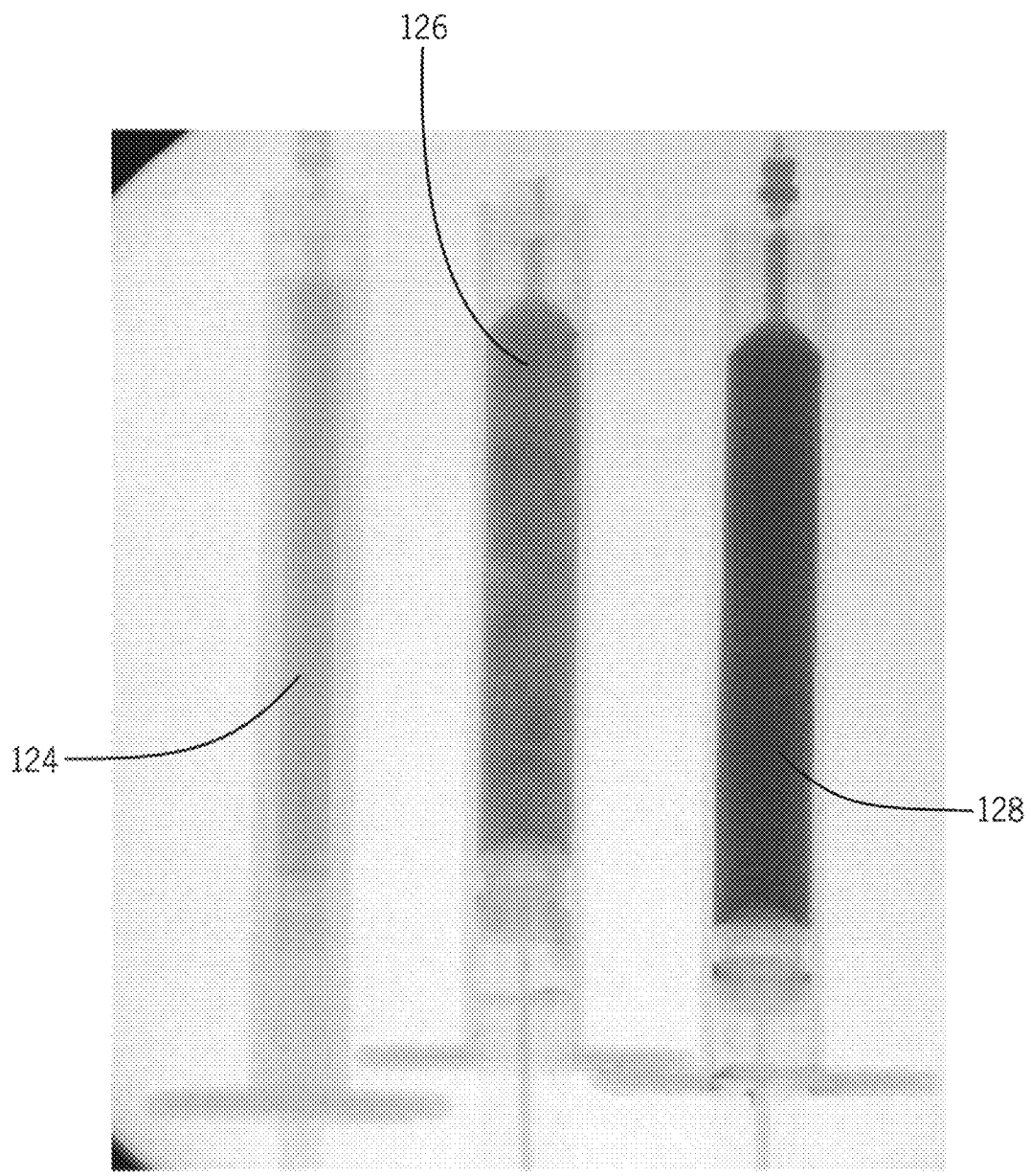
FIG. 11 illustrates a series of ex vivo ultrasound images of three different nanocomposite compositions in accordance with aspects of the disclosure.
Figure 12:
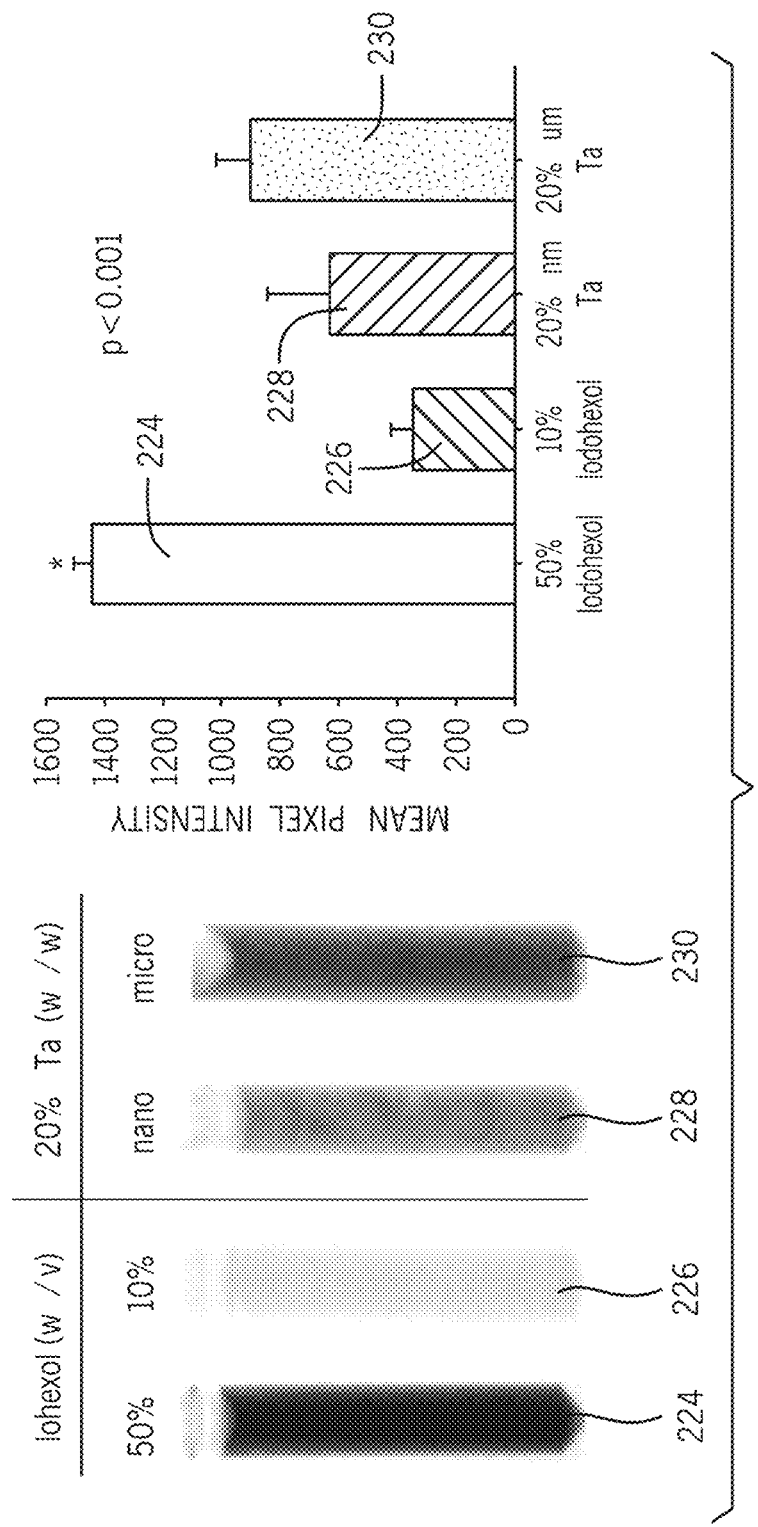
FIG. 12 illustrates a series of ex vivo x-ray fluoroscopic images acquired using a clinically used C-Arm system and quantitative imaging data for four different by a nancomposite composition in accordance with aspects of the disclosure.
Figure 14:
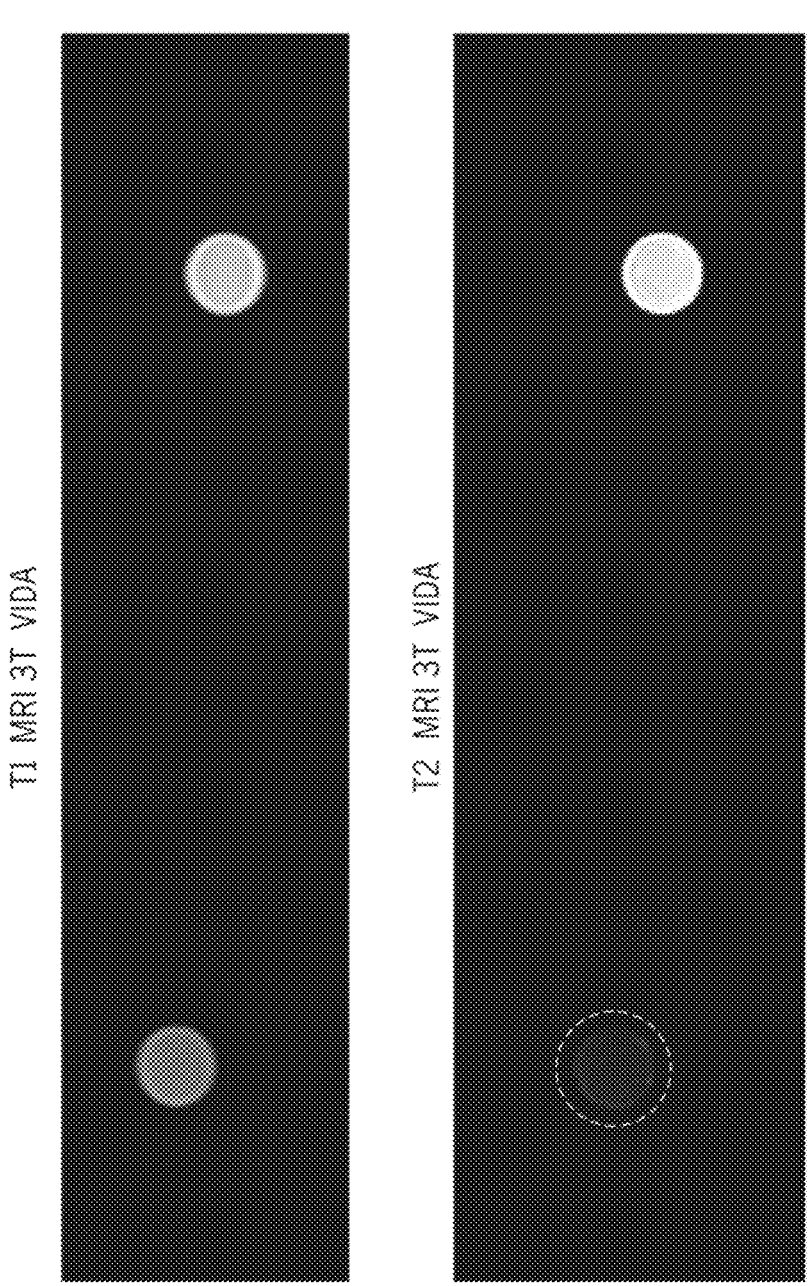
FIG. 14 illustrates a series of magnetic resonance (MRI) T1 and T2 weighted axial images of a nanocomposite composition, doped with contrast agent, inside a tube.

In some aspects of the invention, a nanocomposite composition used in accordance with any of the above-described methods can be visible across various imaging modalities. For example, in some embodiments, the composition with a particular contrast agent formulation can be easily visible and free of artifacts when imaged using x-Ray (e.g., as shown in FIG. 12), US (e.g., as shown in FIG. 11), CT (e.g., as shown in FIGS. 8-9 and 14), and MRI (e.g., as shown in FIG. 14). This formulation, by allowing for visualization of the composition, can aid in the assessment of outcomes. Example contrast agents can include, but are not limited to, tantalum and iohexol.

Accordingly, in some embodiments, nanocomposite compositions can be visible across all four main imaging modalities: ultrasound, fluoroscopy, CT, and MRI. For example, FIG. 11 shows an ultrasound image of three different nanocomposite compositions 124, 126, and 128, each of which is doped with a different concentration of contrast agent. As illustrated in FIG. 11, the nanocomposite composition 128 contains the greatest concentration of contrast agent, the nanocomposite composition 126 contains the second greatest concentration of contrast agent, and the nanocomposite composition 124 has the lowest concentration of contrast agent.

In another example, x-ray fluoroscopy imaging was used to titrate contrast agent concentration levels within nanocomposite compositions to determine whether they can be comfortably visualized by x-ray. FIG. 12 shows an image of four nanocomposite compositions, and a graph of the mean pixel intensity of each of the four nanocomposite compositions based on results from fluoroscopy imaging (i.e., x-ray imaging). Specifically, FIG. 12 illustrates nanocomposite compositions 224, 226, 228, and 230. The nanocomposite composition 224 is doped with a concentration of 50% w/v iohexol contrast agent; the nanocomposite composition 226 is doped with a concentration of 10% w/v iohexol; the nanocomposite composition 228 contains nanoclay particles and is doped with a concentration of 20% w/v tantalum (Ta); and the nanocomposite composition 230 contains microparticles and is doped with a concentration of 20% w/v Ta.

These shear-thinning biomaterials doped with contrast agents resulted in marked x-ray image enhancement. Furthermore, quantitative densitometry analysis revealed variable and concentration-dependent pixel intensities of each agent. More specifically, FIG. 12 also shows a graph indicating the results of fluoroscopy imaging of each of the nanocomposite compositions 224, 226, 228, 230 with respect to mean pixel intensity. The nanocomposite composition 224 had the greatest mean pixel intensity in the resulting images, followed by the nanocomposite composition 230, the nanocomposite composition 228, and lastly the nanocomposite composition 226 (i.e., the nanocomposite composition 226 had the lowest mean pixel intensity).

Figure 13:
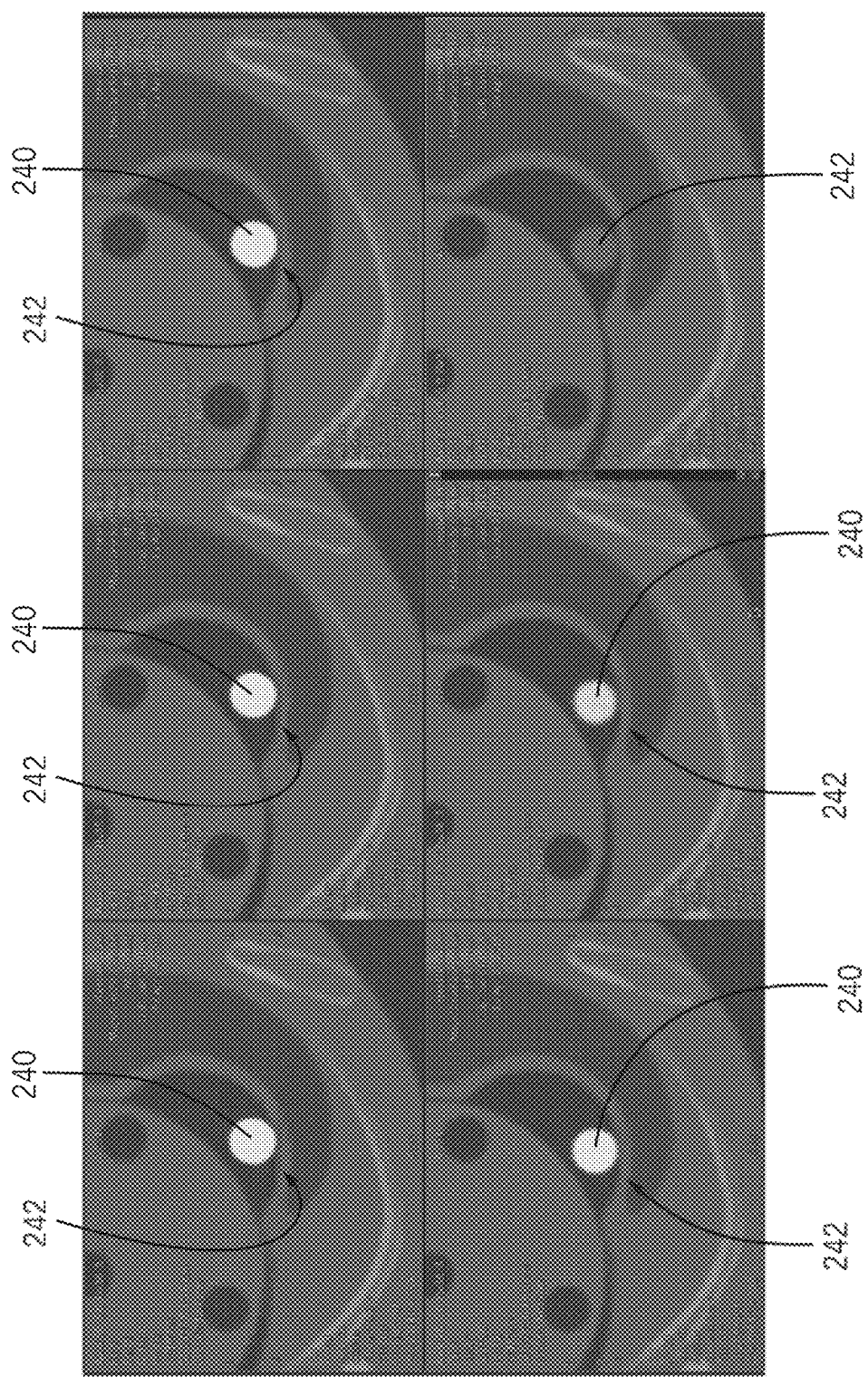
FIG. 13 illustrates a series of ex vivo CT images of a nanocomposite composition within a tube inside a human phantom.

Additionally, FIG. 13 illustrates a series of CT images each showing a nanocomposite composition 240, doped with a contrast agent in accordance with the embodiments described above, occluding a fallopian tube 242 in a human phantom. More specifically, the images show nanocomposite compositions with varying concentrations of tantalum loaded inside 3-ml syringe tubes and placed inside a clinical chest-phantom. The axial views show each composition 240 within the respective tube (bright circles) with concentration-dependent radio-opacity and without any imaging artifact. As shown in FIG. 13, the nanocomposite composition 240 hugs the wall of the fallopian tube 242 along its entire aspect. The last image in the series of images shows the fallopian tube 242 unoccluded (shown as a shaded grey circle), as the image was acquired past the location of the nanocomposite composition 240. In some aspects, it was shown that nanocomposite compositions having 20% (w/v) doped tantalum provided an optimized formulation to balance visualization without any potential artifacts. For example, concentrations of greater than 20% tantalum (w/v) added to a STB may lead to CT artifacts.

FIG. 14 shows a series of images of T1 and T2 weighted MRI sequences for a nanocomposite composition having 20% (w/v) Tantalum microparticles inside a tube. As shown, the T1 and T2 weighted MRI images were free of artifacts and demonstrated clear enhancement. Specifically, enhanced nanocomposite visibility was achieved in the T2-weighted MR-sequence, as shown by the evident visibility and substantial hypointensity on the image.

As illustrated above, FIGS. 8-14 demonstrate that various nanocomposite compositions can be viewed, free of artifacts, across four major imaging systems: CT, MRI, fluoroscopy, and ultrasound. Specifically, in some cases, a nanocomposite composition having, for example, 20% (w/v) doped Tantalum can be easily viewed and is free of artifacts on all of these imaging systems (e.g., CT, MRI, fluoroscopy, and ultrasound). This can be especially helpful to be able to effectively track the composition before a procedure, during the procedure, and after the procedure (e.g., to ensure that the respective tube remains occluded). By way of example, once the nanocomposite composition has been placed in the fallopian tube (or other portion of a subject's anatomy), any of the four imaging modalities can be used to verify the location of the nanocomposite composition. Additionally, in some embodiments, the nanocomposite composition can be preloaded in a catheter (e.g., catheter 18). The preloaded catheter, can then be imaged using the four imaging modalities described above, such that the preloaded catheter can be guided to the desired location (e.g., the fallopian tube). Accordingly, a nanocomposite composition having, for example, 20% (w/v) doped tantalum can be imaged within a fallopian tube, vas deferens, or within any vessel of a subject, free of artifacts to assist with visualizing the vessel before, during, or after a procedure.

In accordance with the present invention, a "therapeutically effective amount" of a composition, with respect to the subject method of treatment, refers to an amount of the composition(s) in a preparation which, when administered as part of a desired dosage regimen (to a patient or a subject, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. As used herein, the term "treating" or "treatment" includes reversing, reducing, or arresting one or more of the symptoms, clinical signs, and underlying pathology of a condition in a manner to improve or stabilize a patient's condition.

Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The present invention has been described in terms of one or more preferred embodiments, and it should be appreciated that many equivalents, alternatives, variations, and modifications, aside from those expressly stated, are possible and within the scope of the invention.

The invention claimed is:

1. A method of reversible birth control in a subject, the method comprising:
   administering a biomaterial into a reproductive organ of a subject, wherein the biomaterial is a shear-thinning nanocomposite; wherein the shear-thinning nanocomposite comprises silicate nanoparticles and poly(ethylene) oxide.

2. The method of claim 1, wherein the reproductive organ is one of a fallopian tube, a uterus, or a vas deferens.

3. The method of claim 1, wherein administering the biomaterial includes:
   applying pressure to the biomaterial to cause the biomaterial to flow, in a gel-like state, into the reproductive organ; and
   stopping application of the applied pressure to the biomaterial to cause the biomaterial to change from the gel-like state to a solid state within the reproductive organ.

4. The method of claim 1, wherein the reproductive organ is a fallopian tube, and administering the biomaterial includes inserting a catheter through an intrauterine cavity of the subject until a tip of the catheter reaches the subject's fallopian tube; and administering the biomaterial through the catheter.

5. The method of claim 4 and further comprising pre-loading the catheter with the biomaterial prior to inserting the catheter.

6. The method of claim 1, wherein administering the biomaterial includes inserting a needle percutaneously until the needle reaches the reproductive organ; and administering the biomaterial through the needle.

7. The method of claim 1, wherein the biomaterial is a shear-thinning nanocomposite in combination with a therapeutic agent, wherein the therapeutic agent is one of a chemotherapy agent, an antimicrobial agent, an adhesive agent, an anti-inflammatory agent, a regenerative agent, a hemostatic agent, a steroid, an anti-allergic agent, an anesthetic, an immunosuppressant, and an anti-fungal agent.

8. The method of claim 1 and further comprising reversing the birth control by removing the biomaterial from the reproductive organ.

9. The method of claim 8, wherein removing the biomaterial comprises applying a negative pressure to the biomaterial to cause the biomaterial to change from the solid state back to the gel-like state and to flow out from the reproductive organ.

10. The method of any one of claims 1-9 and further comprising imaging the reproductive organ while administering the biomaterial to guide the administration.

11. The method of claim 1, wherein the poly(ethylene) oxide has a molecular weight of about 10,000 to about 30,000.

12. The method of claim 11, wherein the poly(ethylene) oxide has a molecular weight of about 20,000.

13. The method of any one of claims 1-9 and 11-12, wherein the shear-thinning nanocomposite comprises:
about 0.5% to about 10.0% (w/v %) of silicate nanoparticles and about 4.0% to about 7.0% (w/v %) of poly(ethylene) oxide.

14. The method of any one of claims 1-9 and 11-12, wherein the shear-thinning nanocomposite comprises:
about 1.0% to about 5.0% (w/v %) of silicate nanoparticles and about 5.0% to about 6.0% (w/v %) of poly(ethylene) oxide.

15. The method of any one of claims 1-9 and 11-12, wherein the shear-thinning nanocomposite further comprises deionized water.

16. The method of any one of claims 1-9 and 11-12, wherein the shear-thinning nanocomposite further comprises an imaging agent.

17. The method of claim 16, wherein the imaging agent includes one or tantalum or iohexol.

18. The method of claim 16, wherein the imaging agent is configured so that the shear-thinning nanocomposite is visible when imaged using at least one of ultrasound, fluoroscopy, computerized tomography, or magnetic resonance imaging.

19. The method of any one of claims 1-9 wherein the shear-thinning nanocomposite further comprises gelatin.

* * * * *

UNITED STATES PATENT AND TRADEMARK OFFICE
CERTIFICATE OF CORRECTION

Page 1 of 1

PATENT NO. : 12,246,086 B2
APPLICATION NO. : 17/442444
DATED : March 11, 2025
INVENTOR(S) : Rahmi Oklu et al.

It is certified that error appears in the above-identified patent and that said Letters Patent is hereby corrected as shown below:

In the Specification

Column 1, Line 15, please remove "N/A." and insert the following government support clause:
--This invention was made with government support under HL137193 awarded by the National Institutes of Health. The government has certain rights in the invention.--

Signed and Sealed this
Seventh Day of October, 2025

John A. Squires
*Director of the United States Patent and Trademark Office*